United States Patent [19]
Grubbs et al.

[11] Patent Number: 5,831,108
[45] Date of Patent: Nov. 3, 1998

[54] HIGH METATHESIS ACTIVITY RUTHENIUM AND OSMIUM METAL CARBENE COMPLEXES

[75] Inventors: Robert H. Grubbs, Pasadena, Calif.; Peter Schwab, Bad Durkheim, Germany; Sonbinh T. Nguyen, Evanston, Ill.

[73] Assignee: California Institute of Technology, Pasadena, Calif.

[21] Appl. No.: 693,789

[22] Filed: Jul. 31, 1996

Related U.S. Application Data

[60] Provisional application No. 60/001,862, Aug. 3, 1995 and provisional application No. 60/003,973 Sep. 19, 1995.

[51] Int. Cl.$^6$ .............................. C07F 9/00; C07F 15/00
[52] U.S. Cl. ......................... 556/21; 556/136; 556/137; 502/152; 502/162
[58] Field of Search ........................... 556/21, 136, 137; 502/152, 162

[56] References Cited

U.S. PATENT DOCUMENTS

| | | | |
|---|---|---|---|
| 4,883,851 | 11/1989 | Grubbs et al. | 526/268 |
| 4,945,135 | 7/1990 | Grubbs et al. | 525/338 |
| 4,945,141 | 7/1990 | Grubbs et al. | 526/90 |
| 4,945,144 | 7/1990 | Grubbs et al. | 526/268 |
| 5,198,511 | 3/1993 | Brown-Wensley et al. | 526/113 |
| 5,296,566 | 3/1994 | Brown-Wensley et al. | 526/171 |
| 5,312,940 | 5/1994 | Grubbs et al. | 526/136 |
| 5,342,909 | 8/1994 | Grubbs et al. | 526/171 |

OTHER PUBLICATIONS

Brown–Winsley, K.A., et al., "C$_2$TiCH$_2$ Complexes In Synthetic Applications", Pure Appl. Chem. 55, 1733–1744 (1983).

Collman, J.P., et al., "Radical Mechanism For the Decomposition of RuOPE (CH$_2$CH$_3$)$_2$. Determination of the Metal–Bond Dissociation Energy", J. Am. Chem. Soc. 108, 1332–1333) (1986).

(List continued on next page.)

Primary Examiner—Porfirio Nazario-Gonzalez
Attorney, Agent, or Firm—Limbach & Limbach L.L.P.

[57] ABSTRACT

Ruthenium and osmium carbene compounds that are stable in the presence of a variety of functional groups and can be used to catalyze olefin metathesis reactions on unstrained cyclic and acyclic olefins are disclosed. Also disclosed are methods of making the carbene compounds. The carbene compounds are of the formula

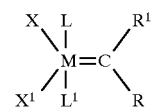

where M is Os or Ru; R$^1$ is hydrogen; R is selected from the group consisting of hydrogen, substituted or unsubstituted alkyl, and substituted or unsubstituted aryl; X and X$^1$ are independently selected from any anionic ligand; and L and L$^1$ are independently selected from any neutral electron donor. The ruthenium and osmium carbene compounds of the present invention may be synthesized using diazo compounds, by neutral electron donor ligand exchange, by cross metathesis, using acetylene, using cumulated olefins, and in a one-pot method using diazo compounds and neutral electron donors. The ruthenium and osmium carbene compounds of the present invention may be used to catalyze olefin metathesis reactions including, but not limited to, ROMP, RCM, depolymerization of unsaturated polymers, synthesis of telechelic polymers, and olefin synthesis.

22 Claims, 2 Drawing Sheets

OTHER PUBLICATIONS

Aquero, A. et al., "Tungsten Wittig Reagents:An Efficient Synthesis of . . .", J. Chem. Soc. Commun. 531–533 (1986).

Novak, B., et al., "The Ring Opening Metathesis Polymerization of 7–oxabicyclo [2.2.2] Hept–5 Ene Derivatives: A New Acyclic Polymeric Ionophore", Jacs, vol. 110, 960–961 (1988).

Schlund, R., et al., "Direct Polymerization of Acetylene to Give Living Polyenes", J. Am. Chem. Soc. 111, No. 20 (1989).

Park, L.Y., et al., "Preparation of Disccrete Polyenes and Norbornene–Polyene Block Copolymers Using Mo (CH–t–Bu) (NAr) (O–t–BU)$_2$ as the Initiator", Macromolecules 24, 3489–3495 (1991).

Wagener, K. B., et al., "Acyclic Diene Metathesis (ADMET) Polymerization", Macromolecules 24, 2649–2657 (1991).

Bazan, G., et al., "Synthesis and Kinetics of Decomposition of Tungsten (VI) and Molybdenum (VI) 2–Oxametallacyclobutane Complexes and the X–Ray Structure of trans–Mo [CH (t–Bu)CH(C$_6$F$_5$)O] (NAr) (O–t–Bu)2", J. Organometallics Chem. 10, 1062–1067 (1991).

Schwab, P., et al., "A Series of Well–Defined Metathesis Catalysts—Synthesis of [RuCI$_2$(=CHR') (PR$_3$) $_2$] and its Reactions", Agnew. Chem. Int. Ed. Engl./ 34 2039–2041 (1995).

Schwab, P., et al., "Synthesis and Applications of RuCI$_2$ (=CHR') (PR$_3$)2: The Influence of the Alkylidene Moiety on Metathesis Activity", J. Am. Chem. Soc. 118, 100–110 (1996).

Burrell et al., Synthesis and Reactions of Ru(=CH$_2$) Cl (No) (PPh$_3$)$_2$, A Stable Terminal MethyleneComplex and the Crystal Structure of Ru(CH$_2$PPF$_2$)$_2$(n$^2$–C$_2$F$_4$Cl (NO) (PPH$_3$), J. Chem. Soc., Dalton Trans., pp. 609–614.

Ivin, K.J. "Olefin Metathesis", 1983, Academic Press, pp. vii–x, 34–36.

McGrath et al., "Aqueous Ring–Opening Metathesis Polymerization of 7–Oxanorborene Derivatives Using Ruthenium Catalysts", 1990, pp. 525–536.

Novak et al., "Catalytic Organometalic Chemistry in Water: The Aqueous Ring–Opening Metathesis Polymerization of 7–Oxanorborene Derivatives", 1988, JACS, vol. 110,pp. 7542–7543g.

Hillmyer et al., "The Aqueous Ring–Opening Metathesis Polymerization of exo–N–Methyl–7–oxabicyclo [2.2.1] hept–5–ene–2, 3–dicarbonximide" 1991, pp. 162–163.

Carter et al., "Review of the Chemistry of Cyclopropane Compounds", Apr. 20, 1964, pp. 497–525.

Schmidbaur et al., "Ylide Chemistry: An Account of Structural, Conformational and Redox Investigations" 1983m pp. 167–170.

"Metathesis of Functionalized Olefin", J. of Molecules Catalysis, 15 (1982), pp. 35–45.

Bruce et al., "Cyclopentadienyl–Ruthenium and –osmium Chemistry. Some Reactions ofSubstituted Vinylidene Complexes," J. Organometallic Chem. 171:C5–C8 (1979).

M.H.L. Green et al., "Carbene Complexes of Iron, Molybdenum, and Ruthenium: A NewRoute to Metal–Carbene Derivatives," J. Chem. Soc. (A) 794–797 (1971).

H. Le Bozec et al., "A New Route to Vinylcarbene Metal Complexes in One Step from2–Propyn–1–ols and Arene Ruthenium(∥) Derivatives," J. Chem. Soc. Chem. Comm. 219–221 (1989).

Grundy et al., "Migratory–Insertion Reactions of Osmium (II) Ethyl Complexes DerivedFrom an Osmium (0) Ethylene Complex," J. Organometallic Chem. 216:255–262 (1981).

Grundy et al., Propionyl Complexes of Ruthenium Derived From the Reaction of Ethylenewith RuHCl (CO)$_2$(PPh$_3$)$_2$ J. Organometallic Chem. 265:77–85 (1984).

Richard R. Schrock, Living Ring–Opening Metathesis Polymerization Catalyzed by Well–Characterized Transition-–Metal Alkylidene Complexes, Acc.Chem.Res. 1990, vol. 23, pp. 158–165.

Gregory C. Fu et al., "Catalytic Ring–Closing Metathesis of Functionalized Dienes by a Ruthenium Carbene Complex" Am. Chem Soc. 1993, pp. 9856–9857.

Robert H. Grubbs et al., "Ring–Opening Metathesis Polymerization Catalysts" Polymer Preprints 1994, 35 (1), p. 688.

Marc A. Hillmyer et al., "The ROMP of COD by a Well-–Defined Metathesis Catalyst in the Presence of a Difunctional Chain Transfer Agent: The Preparation of Hydroxy–Telechelic 1,4–Poly(butadiene)", Polymer Preprints 1993, 34 (2), pp. 388–389.

Marc A. Hillmyer et al., "Preparation of Hydroxytelechelic Poly (butadiene) via Ring–Opening Metathesis Polymerization Employing a Well–Defined Metathesis Catalyst" Am. Chem. Soc. Macromolecules, vol. 26, No. 4, 1992, pp. 872–874.

SonBinh R. Nguyen et al., "Syntheses and Activities of New Single–Component Ruthenium–Based Olefin Metathesis Catalysts" J. Am. Chem Soc. 1993, 115, 9858–9859.

SonBinh R. Nguyen et al., "Ring–Opening Metathesis Polymerization (ROMP) of Norbornene by a Group VIII Carbene Complex in Protic Media", J. Am. Schem. Soc. 1992, 114, 3974–3975.

HIGH METATHESIS ACTIVITY RUTHENIUM AND OSMIUM METAL CARBENE COMPLEXES

The U.S. Government has certain rights in this invention pursuant to Grant No. CHE-8922072 awarded by the National Science Foundation.

This application claims the benefit of U.S. Provisional application Ser. No. 60/001,862, filed Aug. 3, 1995, and U.S. Provisional application Ser. No. 60/003,973, filed Sep. 19, 1995, both of which are incorporated herein by reference.

BACKGROUND

This invention relates to highly active and stable ruthenium and osmium metal carbene complex compounds, their synthesis and use as catalysts for olefin metathesis reactions.

Transition-metal catalyzed C—C bond formation via olefin metathesis is of considerable interest and synthetic utility. Initial studies in this area were based on catalytically active mixtures consisting of transition-metal chlorides, oxides or oxychlorides, cocatalysts such as $EtAlCl_2$ or $R_4Sn$, and promoters including $O_2$, EtOH or PhOH. For example, $WCl_6/EtAlCl_2/EtOH$ 1:4:1. These systems catalyze olefin metathesis reactions, however their catalytic centers are ill-defined and systematic control of their catalytic activity is not possible.

Recent efforts have been directed towards the development of well-defined metathesis active catalysts based on transition metal complexes. The results of research efforts during the past two decades have enabled an in-depth understanding of the olefin metathesis reaction as catalyzed by early transition metal complexes. In contrast, the nature of the intermediates and the reaction mechanism for Group VIII transition metal catalysts have remained elusive. In particular, the oxidation states and ligation of the ruthenium and osmium metathesis intermediates are not known.

Group VIII transition metal olefin metathesis catalysts, specifically ruthenium and osmium carbene complexes, have been described in U.S. Pat. Nos. 5,312,940 and 5,342,909 and U.S. patent application Ser. Nos. 08/282,826 and 08/282,827, all of which are incorporated herein by reference. The ruthenium and osmium carbene complexes disclosed in these patents and applications are of the general formula

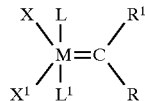

where M is ruthenium or osmium, X and $X^1$ are anionic ligands, and L and $L^1$ are neutral electron donors.

U.S. Pat. Nos. 5,312,940 and 5,342,909 disclose specific vinyl alkylidene ruthenium and osmium complexes and their use in catalyzing the ring opening metathesis polymerization ("ROMP") of strained olefins. In all of the specific alkylidene complexes disclosed in these patents, $R^1$ is hydrogen and R is either a substituted or unsubstituted vinyl group. For example, a preferred vinyl alkylidene complex disclosed in these patents is

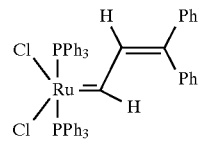

where Ph is phenyl.

U.S. patent application Ser. Nos. 08/282,826 and 08/282,827 disclose specific vinyl alkylidene ruthenium and osmium complexes and their use in catalyzing a variety of metathesis reactions. The catalysts disclosed in these applications have specific neutral electron donor ligands L and $L^1$; namely, phosphines in which at least one substituent is a secondary-alkyl or cycloalkyl group. As in the above U.S. patents, in all of the specific alkylidene complexes disclosed in the patent applications, $R^1$ is hydrogen and R is either a substituted or unsubstituted vinyl group. For example, a preferred vinyl alkylidene complex disclosed in these patent applications is

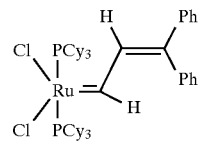

where Cy is cyclohexyl.

Although the vinyl alkylidene complexes disclosed in the above patents and patent applications exhibit high metathesis activity and remarkable stability towards functional groups there are at least two drawbacks to these complexes as metathesis catalysts. First, the preparation of the vinyl alkylidene complexes requires a multi-step synthesis; and second, the vinyl alkylidene complexes have relatively low initiation rates. Both of these aspects of the vinyl alkylidene complexes are undesirable for their use as metathesis catalysts. The multi-step synthesis may be time consuming and expensive and may result in lower product yields. The low initiation rate may result in ROMP polymers with a broad molecular weight distribution and prolonged reaction times in ring closing metathesis ("RCM") reactions.

For the reasons discussed above, there is a need for well-defined metathesis active catalysts that have the following characteristics: first, they are stable in the presence of a wide variety of functional groups; second, they can catalyze a variety of metathesis reactions including the metathesis of acyclic and unstrained cyclic olefins; third, they have a high initiation rate; and fourth, they are easily prepared. Furthermore, there is a need for olefin metathesis catalysts that can catalyze the ROMP of strained and unstrained cyclic olefins to yield polymers of very low polydispersity (i.e., PDI≈1.0) and that can catalyze the RCM of acyclic dienes with short reaction times.

SUMMARY

The present invention meets the above needs and provides well-defined ruthenium and osmium carbene compounds that are stable in the presence of a variety of functional groups and can be used to catalyze olefin metathesis reactions on unstrained cyclic and acyclic olefins. The compounds of the present invention are highly active in metathesis reactions and have high initiation rates.

In one embodiment of the present invention, the ruthenium and osmium carbene compounds have the formula

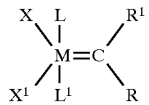

where M may be Os or Ru; $R^1$ is hydrogen; X and $X^1$ may be different or the same and are any anionic ligand; L and $L^1$ may be different or the same and are any neutral electron donor; and R may be hydrogen, substituted or unsubstituted alkyl, or substituted or unsubstituted aryl.

The ruthenium and osmium carbene complexes of the present invention are stable in the presence of a variety of functional groups. A consequence of this is that the alkyl and aryl R group may contain one or more functional groups including alcohol, thiol, ketone, aldehyde, ester, ether, amine, imine, amide, nitro, carboxylic acid, disulfide, carbonate, isocyanate, carbodiimide, carboalkoxy, and halogen groups.

R is preferably hydrogen, $C_1$–$C_{20}$ alkyl, or aryl. The $C_1$–$C_{20}$ alkyl may optionally be substituted with one or more aryl, halide, hydroxy, $C_1$–$C_{20}$ alkoxy, or $C_2$–$C_{20}$ alkoxycarbonyl groups. The aryl may optionally be substituted with one or more $C_1$–$C_{20}$ alkyl, aryl, hydroxyl, $C_1$–$C_5$ alkoxy, amino, nitro, or halide groups.

L and $L^1$ are preferably phosphines of the formula $PR^3R^4R^5$, where $R^3$ is a secondary alkyl or cycloalkyl, and $R^4$ and $R^5$ are aryl, $C_1$–$C_{10}$ primary alkyl, secondary alkyl, or cycloalkyl. $R^4$ and $R^5$ may be the same or different.

L and $L^1$ are most preferably the same and are —P(cyclohexyl)$_3$, —P(cyclopentyl)$_3$, or —P(isopropyl)$_3$.

X and $X^1$ are most preferably the same and are chlorine.

In another embodiment of the present invention, the ruthenium and osmium carbene compounds have the formula

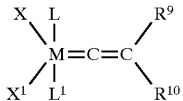

where M may be Os or Ru; X and $X^1$ may be different or the same and are any anionic ligand; L and $L^1$ may be different or the same and are any neutral electron donor; and $R^9$ and $R^{10}$ may be different or the same and may be hydrogen, substituted or unsubstituted alkyl, or substituted or unsubstituted aryl. The $R^9$ and $R^{10}$ groups may optionally include one or more of the following functional groups: alcohol, thiol, ketone, aldehyde, ester, ether, amine, imine, amide, nitro, carboxylic acid, disulfide, carbonate, isocyanate, carbodiimide, carboalkoxy, and halogen groups.

The ruthenium and osmium carbene compounds of the present invention may be used to catalyze olefin metathesis reactions including, but not limited to, ROMP, RCM, depolymerization of unsaturated polymers, synthesis of telechelic polymers, and olefin synthesis.

In the ROMP reaction, a compound according to the present invention is contacted with a cyclic olefin to yield a ROMP polymer product. In the RCM reaction, a compound according to the present invention is contacted with a diene to yield a ring-closed product. In the depolymerization reaction, a compound according to the present invention is contacted with an unsaturated polymer in the presence of an acyclic olefin to yield a depolymerized product. In the synthesis of telechelic polymers, a compound according to the present invention is contacted with a cyclic olefin in the presence of an α,ω-difunctional olefin to yield a telechelic polymer. In the olefin synthesis reaction, a compound according to the present invention is contacted with one or two acyclic olefins to yield self-metathesis or crossmetathesis olefin products.

Since the ruthenium and osmium carbene compounds of the present invention are stable in the presence of a variety of functional groups, the olefins involved in the above reactions may optionally be substituted with one or more functional groups including alcohol, thiol, ketone, aldehyde, ester, ether, amine, imine, amide, nitro, carboxylic acid, disulfide, carbonate, isocyanate, carbodiimide, carboalkoxy, and halogen groups.

The above reactions may be carried out in aqueous, protic, or organic solvents or mixtures of such solvents. The reactions may also be carried out in the absence of a solvent. The reactants may be in the gas phase or liquid phase.

The ruthenium and osmium carbene compounds of the present invention may be synthesized using diazo compounds, by neutral electron donor ligand exchange, by cross metathesis, using acetylene, using cumulated olefins, and in a one-pot method using diazo compounds and neutral electron donors.

BRIEF DESCRIPTION OF DRAWINGS

The invention will be better understood by reference to the appended figures wherein.

DETAILED DESCRIPTION

Figure 1A:
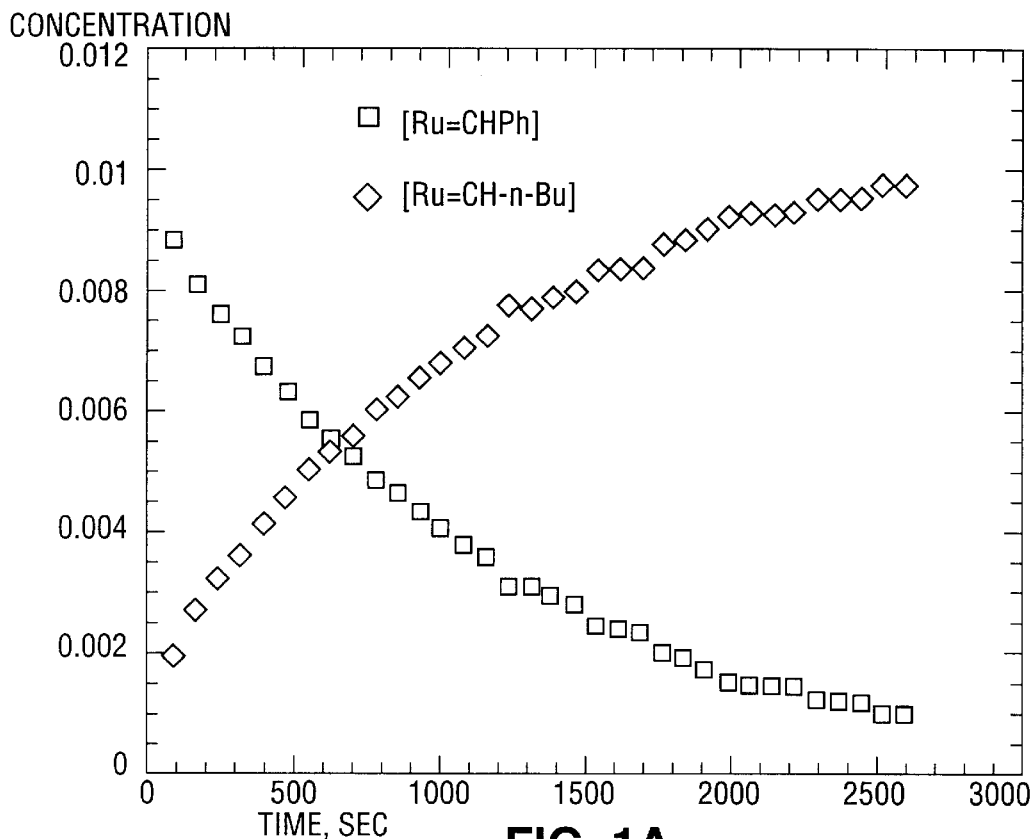
FIGS. 1A and 1B are representative kinetic plots for acyclic metathesis of 1-hexene with $RuCl_2$(=CHPh) $(PCy_3)_2$ (complex 10) at 0° C.

The abbreviations Me, Ph, $^iPr$ or i-Pr, Cy, Cp, n-Bu, and THF refer to methyl, phenyl, isopropyl, cyclohexyl, cyclopentyl, n-butyl, and tetrahydrofuran, respectively.

While previous investigations have explored the influence of the neutral electron donor and anionic ligands (i.e. L, $L^1$, X, and $X^1$) on the stability and utility of the ruthenium and osmium carbene complexes, the effect of variation of the alkylidene moieties (R and $R^1$) had not been studied. By studying the effect of these substituents, it has been discovered that ruthenium and osmium complexes containing the specific alkylidene moieties of the present invention have unexpectedly high initiation rates compared to the vinyl alkylidene complexes previously described. Quantitative data is included below that demonstrates that the initiation rates of the complexes of the present invention are approximately a thousand times higher than the initiation rates of the corresponding vinyl alkylidene complexes. In addition to having unexpectedly high initiation rates, the complexes of the present invention are stable in the presence of a variety of functional groups and have high metathesis activity allowing them to catalyze a variety of metathesis reactions including metathesis reactions involving acyclic and unstrained cyclic olefins.

The compounds of the present invention are ruthenium and osmium alkylidene complexes of the general formula

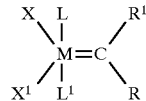

where $R^1$ is hydrogen and R is selected from the specific group described below. Generally X and $X^1$ can be any anionic ligand and L and $L^1$ can be any neutral electron donor. Specific embodiments of X, $X^1$, L, and $L^1$ are described in detail in U.S. Pat. Nos. 5,312,940 and 5,342,909 and U.S. patent application Ser. Nos. 08/282,826 and 08/282,827.

R may be hydrogen, substituted or unsubstituted alkyl, or substituted or unsubstituted aryl. The ruthenium and osmium carbene complexes of the present invention are stable in the presence of a variety of functional groups. A consequence of this is that the alkyl and aryl R groups may contain a variety of functional groups including alcohol, thiol, ketone, aldehyde, ester, ether, amine, imine, amide, nitro, carboxylic acid, disulfide, carbonate, isocyanate, carbodiimide, carboalkoxy, and halogen groups.

In a prefered embodiment R is hydrogen, $C_1-C_{20}$ alkyl, or aryl. The $C_1-C_{20}$ alkyl may optionally be substituted with one or more aryl, halide, hydroxy, $C_1-C_{20}$ alkoxy, or $C_2-C_{20}$ alkoxycarbonyl groups. The aryl may optionally be substituted with one or more $C_1-C_{20}$ alkyl, aryl, hydroxyl, $C_1-C_5$ alkoxy, amino, nitro, or halide groups. In a more prefered embodiment, R is hydrogen, $C_1-C_4$ alkyl, phenyl, $C_1-C_4$ alkyl substituted with one or more groups selected from the group consisting of halide, hydroxy, and $C_2-C_5$ alkoxycarbonyl, or phenyl substituted with one or more groups selected from the group consisting of $C_1-C_5$ alkyl, $C_1-C_5$ alkoxy, amino, nitro, and halide.

In a more preferred embodiment R may be hydrogen, methyl, ethyl, n-butyl, iso-propyl, $-CH_2Cl$, $-CH_2CH_2CH_2OH$, $-CH_2OAc$, phenyl. The phenyl may optionally be substituted with a chloride, bromide, iodide, fluoride, $-NO_2$, $-NMe_2$, methoxy, or methyl group. In a more prefered embodiment, the phenyl is para-substituted.

In a most prefered embodiment R is phenyl.

Preferred complexes of the present invention include

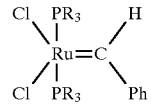

where R is cyclohexyl, cyclopentyl, iso-propyl, or phenyl.

The most preferred complex of the present invention is

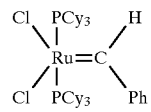

The ruthenium and osmium alkylidene complexes of the present invention may be synthesized by a variety of different methods including those taught in P. Schwab et al. Angew. Chem. Int. Ed. Engl. 34, 2039–2041 (1995), and P. Schwab et al. J. Am. Chem. Soc. 118, 100–110 (1996), both of which are incorporated herein by reference.

The ruthenium and osmium complexes of the present invention may be synthesized by alkylidene transfer from diazoalkanes. This synthetic method may generally be written as

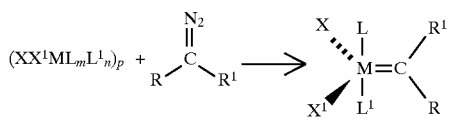

where M, X, $X^1$, L, $L^1$, R and $R^1$ are as described above; m and n are independently 0–3 such that m+n=3; and p is a positive integer. In the diazo synthesis, a compound of the formula $(XX^1ML_nL^1_m)_p$ is contacted with a diazo compound of the formula $RC(N_2)R^1$ to yield an alkylidene according to the present invention.

The ruthenium and osmium complexes of the present invention may also be synthesized by neutral electron donor ligand exchange as disclosed in U.S. Pat. Nos. 5,312,940 and 5,342,909 and U.S. patent application Ser. Nos. 08/282,826 and 5 08/282,827.

The ruthenium and osmium complexes of the present invention may also be synthesized by cross metathesis. This method may generally be written as

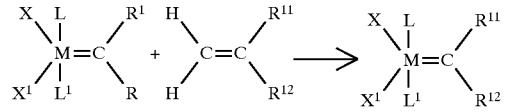

where $R^{11}$ and $R^{12}$ may be the same or different and may be hydrogen, substituted or unsubstituted alkyl, or substituted or unsubstituted aryl.

The ruthenium and osmium complexes of the present invention may also be synthesized using acetylene reactants. This method may generally be written as

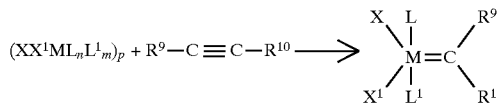

In the acetylene synthesis, a compound of the formula $(XX^1ML_nL^1_m)_p$ is reacted with an acetylene compound of the formula $R^9CCR^{10}$, to yield an alkylidene according to the present invention. $R^9$ and $R^{10}$ may be the same or different and may be hydrogen, substituted or unsubstituted alkyl, or substituted or unsubstituted aryl.

The ruthenium and osmium complexes of the present invention may also be synthesized using cumulated olefins. This method may generally be written as

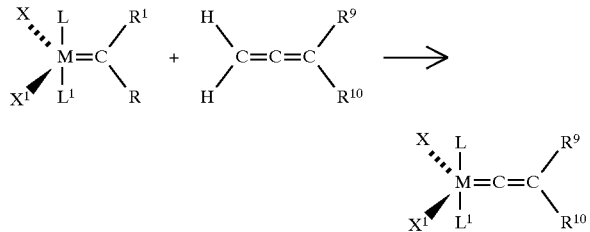

The ruthenium and osmium complexes of the present invention may also be synthesized by a "one pot" method that can generally be written as

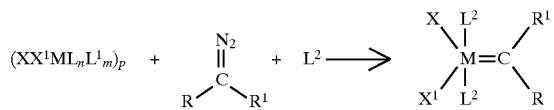

In this method, a compound of the formula $(XX^1ML_nL^1_m)_p$ is contacted with a diazo compound of the formula $RC(N_2)R^1$ in the presence of a neutral electron donor $L^2$ to yield an alkylidene compound according to the present invention.

The catalysts of the present invention are highly active in metathesis reactions and may be used to catalyze a variety of metathesis reactions including, but not limited to, ROMP of strained and unstrained cyclic olefins, RCM of acyclic dienes, self- and cross-metathesis reactions involving at least one acyclic or unstrained cyclic olefin, depolymerization of olefinic polymers, acyclic diene metathesis polymerization ("ADMET"), alkyne polymerization, carbonyl olefination, and preparation of telechelic polymers.

ROMP, RCM, cross metathesis, depolymerization, and telechelic polymer reactions have been described in detail in U.S. patent application Ser. No. 08/282,827. Those skilled in the art can readily identify the appropriate conditions for carrying out these reactions using the complexes of the present invention. Any specific differences between the reactions disclosed in patent application Ser. No. 08/282,827 and those of the present invention are noted in the detailed descriptions given below.

Alkyne polymerization is described by R. Schlund et al. in *J. Am. Chem. Soc.* 1989, 111, 8004–8006, and by L. Y. Park et al. in *Macromolecules* 1991, 24 3489–3495, both of which are incorporated herein by reference. Carbonyl olefination is described by K. A. Brown-Wensley et al. in *Pure Appl. Chem.* 1983, 55, 1733–1744, by A. Aguero et al. in *J. Chem. Soc., Chem. Commun.* 1986, 531–533, and by G. C. Bazan et al. in *Organometallics* 1991, 10, 1062–1067, all of which are incorporated herein by reference. ADMET is described by K. B. Wagener et al. in *Macromolecules* 1991, 24, 2649–2657, which is incorporated herein by reference. Those skilled in the art can readily identify the appropriate conditions for carrying out these reactions using the complexes of the present invention.

We now describe specific examples of the synthesis and olefin metathesis reactions described above. For clarity, detailed reaction conditions and procedures are described in the final, "Experimental Procedures" section.

SYNTHESIS OF ALKYLIDENE COMPLEXES

Synthesis of $RuCl_2(=CHR)(PPh_3)_2$ via Alkylidene Transfer from Diazoalkanes (Complexes 1–9)

The alkylidene complexes of the present invention may be synthesized by the reaction of $RuCl_2(PPh_3)_3$ with alkyl, aryl, and diaryldiazoalkanes. Generally, the synthesis reactions involve a spontaneous $N_2$ evolution at $-78°$ C., indicating rapid reaction of $RuCl_2(PPh_3)_3$ with diazoethane, diazopropane or a para-substituted aryldiazoalkane of the formula p-$C_6H_4XCHN_2$ to give $RuCl_2(=CHR)(PPh_3)_2$ (R=Me [complex 1], Et [complex 2]) and $RuCl_2(=CH$-p-$C_6H_4X)(PPh_3)_2$ (X=H [complex 3], $NMe_2$ [complex 4], OMe [complex 5], Me [complex 6], F [complex 7], Cl [complex 8], $NO_2$ [complex 9]), respectively (eq. 1). However, no reaction was observed with diphenyldiazomethane or 9-diazofluorene at RT, and reaction with diazomethane led to a complex mixture of unidentified products.

Complexes 1–9 were isolated in 80–90% yield as green air-stable solids. In all of these reactions, transfer of the alkylidene moiety from the diazo compound to ruthenium was clearly indicated by the characteristic downfield-resonances of $H_\alpha$ and $C_\alpha$ of the alkylidene moiety. Table I below lists selected NMR data for complexes 3–9.

TABLE I

| Complex | X | $H_\alpha$ | $J_{HP}$(Hz) | $C_\alpha$ | $J_{PC}$(Hz) |
|---|---|---|---|---|---|
| 3 | H | 19.56[a] | 10.2 | 310.12 | 11.4 |
| 4 | $NMe_2$ | 18.30 | 6.1 | 309.68 | 11.4 |
| 5 | OMe | 19.38[a] | 8.7 | 309.20 | 10.7 |
| 6 | Me | 19.55[a] | 9.6 | 309.17 | 10.9 |
| 7 | F | 19.24 | 9.0 | 307.51 | 11.4 |
| 8 | Cl | 19.27 | 9.2 | 307.34 | 10.6 |
| 9 | $NO_2$ | 19.47 | 10.8 | 313.43 | 11.2 |

Spectra taken in $CD_2Cl_2$ (in ppm) unless indicated otherwise.
[a]In $C_6D_6$ (in ppm).

In analogy to the structurally characterized vinyl alkylidene $RuCl_2(=CH-CH=CPh_2)(PPh_3)_2$ (Complex A), these resonances appear as triplets due to $^{31}P$ coupling. These spectroscopic data suggest that the phosphines are mutually trans and that the alkylidene unit lies in the P-Ru-P-plane. Additionally, the chemical shifts of $H_\alpha$ and $C_\alpha$ in complexes 3–9 are downfield compared to $RuCl_2(=CH-CH=CPh_2)(PPh_3)_2$ (Complex A) ($\delta$ $H_\alpha$=17.94, $C_\alpha$=288.9 ppm), possibly attributed to the relatively reduced conjugation of the alkylidene unit of complexes 3–9. This phenomenon might also be responsible for the relative instability of complexes 1–9 in solution. These complexes decompose within several hours via bimolecular pathways as evidenced by the formation of the corresponding disubstituted olefins RCH=CHR (R=Me, Et, p-$C_6H_4X$).

Synthesis of $RuCl_2(=CH$-p-$C_6H_4X)(PCy_3)_2$ via Phosphine exchange (Complexes 10–16)

To broaden the synthetic utility of the triphenylphosphine catalysts, analogous trialkylphosphine derivatives of complexes 3–9 were prepared by phosphine exchange. Treatment of complexes 3–9 with 2.2 equiv. tricyclohexylphosphine at RT afforded, after work-up, $RuCl_2(=CH$-p-$C_6H_4X)(PCy_3)_2$ (X=H [complex 10], $NMe_2$ [complex 11], OMe [complex 12], Me [complex 13], F [complex 14], Cl [complex 15], $NO_2$ [complex 16]), as purple (complex 11 is green) microcrystalline solids in high yields according to the following reaction:

EQUATION 1

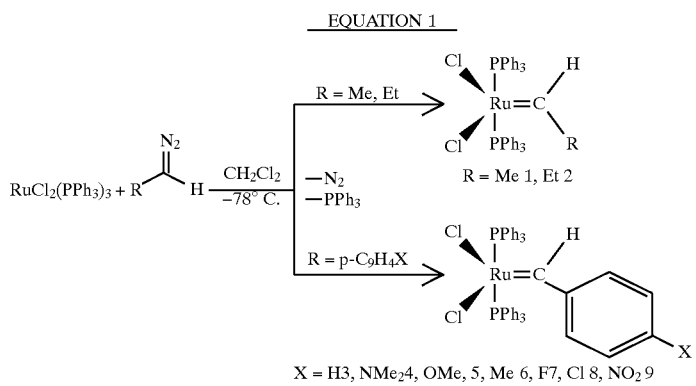

X = H3, $NMe_2$4, OMe, 5, Me 6, F7, Cl 8, $NO_2$ 9

EQUATION 2

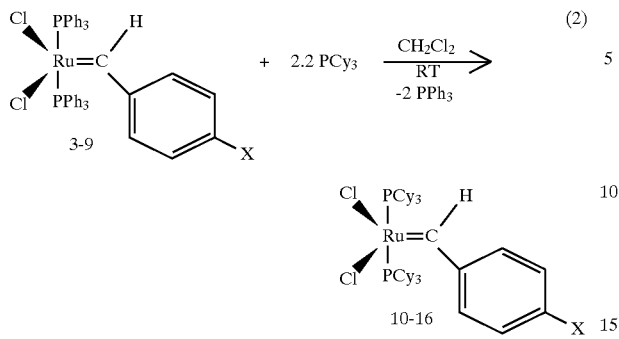

The fully-characterized compounds were air-stable in the solid state and did not show any signs of decomposition in solution ($CH_2Cl_2$ or $C_6H_6$), even when heated to 60° C. or in presence of alcohols, amines or water. Selected solution NMR data for complexes 10–16 are listed in Table II. As can be seen from this data, in contrast to the $PPh_3$ complexes 3–9, no $^{31}P$ coupling was observed for the $H_\alpha$ resonances of complexes 10–16 in the $^1H$ NMR. The chemical shifts of these resonances are dependent on the electronic nature of the X substituent.

TABLE II

| Complex | X | $H_\alpha$ | $C_\alpha$ | $J_{PC}$(Hz) |
|---|---|---|---|---|
| 10 | H | 20.02 | 294.72 | 7.6 |
| 11 | $NMe_2$ | 18.77 | 286.13 | a |
| 12 | OMe | 19.48 | 290.90 | a |
| 13 | Me | 19.80 | 293.86 | 8.3 |
| 14 | F | 19.86 | 291.52 | 8.6 |
| 15 | Cl | 19.98 | 291.46 | 8.0 |
| 16 | $NO_2$ | 20.71 | 289.07 | 7.6 |

Spectra taken in $CD_2Cl_2$ (in ppm).
a broad signal

The lack of $^{31}P$ coupling suggests that the alkylidene moiety is perpendicular to the P-Ru-P-plane as in $RuCl_2$(=CH—CH=$CPh_2$)($PCy_3$)$_2$ (Complex B). Also, the resonance shifts' dependency on the electronic nature of the X substituent suggests a high degree of conjugation between the carbene carbon and the aromatic ring of the benzylidene moiety.

One-pot Synthesis of $RuCl_2$(=CHPh)($PR_3$)$_2$ (Complexes 10, 17 and 18)

Due to the relative instability of the intermediate $RuCl_2$(=CHPh)($PPh_3$)$_2$ (complex 3) in solution, $RuCl_2$(=CHPh)($PCy_3$)$_2$ (complex 10) can be synthesized in 75–80% yield from $RuCl_2$($PPh_3$)$_3$. However, avoiding isolation of complex 3 and adding tricyclohexylphosphine at ≈−50° C. shortly after $RuCl_2$($PPh_3$)$_3$ was treated with phenyldiazomethane, complex 10 can be obtained in nearly quantitative yield in less than 1 hour in a so-called "one pot synthesis". The same procedure can also be applied to the synthesis of more soluble derivatives including $RuCl_2$(=CHPh)($PR_3$)$_2$ where R is Cp (complex 17) or R is $^iPr$ (complex 18) that exhibit comparable metathesis activity, according to the following reaction:

EQUATION 3

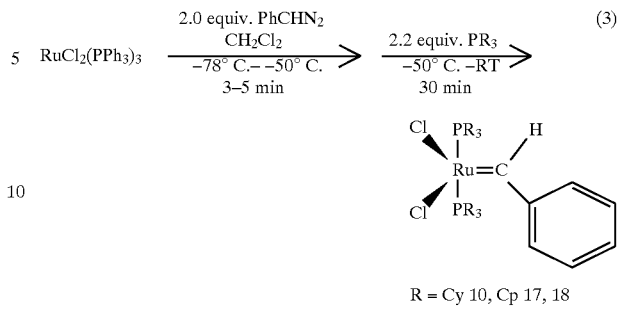

R = Cy 10, Cp 17, 18

Synthesis of Methylidene Complex $RuCl_2$(=$CH_2$)($PCy_3$)$_2$ (Complex 19)

Whereas $RuCl_2$(=CH—CH=$CPh_2$)($PCy_3$)$_2$ (Complex B) reacts with ethylene under 100 psi pressure at 50° C. in $CD_2Cl_2$ within several hours to reach an equilibrium of $RuCl_2$(=CH—CH=$CPh_2$)($PCy_3$)$_2$ (Complex B) and $RuCl_2$(=$CH_2$)($PCy_3$)$_2$ (complex 19) in a ratio of 80:20, benzylidene $RuCl_2$(=CHPh)$PCy_3$)$_2$ (complex 10) is quantitatively converted to the methylidene complex 19 within a few minutes at RT under 14 psi of ethylene (eq. 7).

EQUATION 7

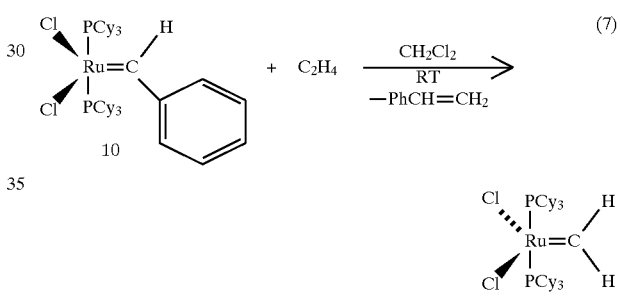

Complex 19 is isolated as a red-purple, air-stable solid. A pentacoordinate ruthenium center may be inferred from the analytic and spectroscopic data. Methylidene complex 19 is less stable in solution than benzylidene complex 10; decomposition is observed after 12 hours in solution ($CH_2Cl_2$, $C_6H_6$). The decomposition rate increases as catalyst solutions are heated. Among all isolated methylidene complexes including $RuCl(NO)(CH_2)(PPh_3)_2$ and Ir=$CH_2$(N($SiMe_2$—$CH_2PPh_2$)$_2$), complex 19 is the first isolable metathesis-active methylidene complex. Complex 19 has a high activity and exhibits a similar stability towards functional groups as benzylidene complex 10, as shown in the ROMP of cyclooctene and 1,5-cyclooctadiene and in ring-closing metathesis of diethyldiallyl malonate.

Synthesis of substituted alkylidene complexes via cross metathesis

The rapid reaction of $RuCl_2$(=CHPh)($PCy_3$)$_2$ (complex 10) with ethylene to give $RuCl_2$(=CHPh)($PCy_3$)$_2$ (complex 19) has prompted extension by the inventors of these metathesis studies to terminal and disubstituted olefins. Although olefin metathesis is an equilibrium process, the kinetic products may be isolated under certain conditions. Indeed, complex 10 is quantitatively converted to the alkylidenes according to the formula $RuCl_2$(=CHR)($PCy_3$)$_2$ [R=Me (complex 20), R=Et (complex 21), R=n-Bu (complex 22)] when reacted with a tenfold excess of propene, 1-butene or 1-hexene, respectively. In each case, an equimolar amount of styrene was formed and spectroscopically identified (eq. 4).

EQUATION 4

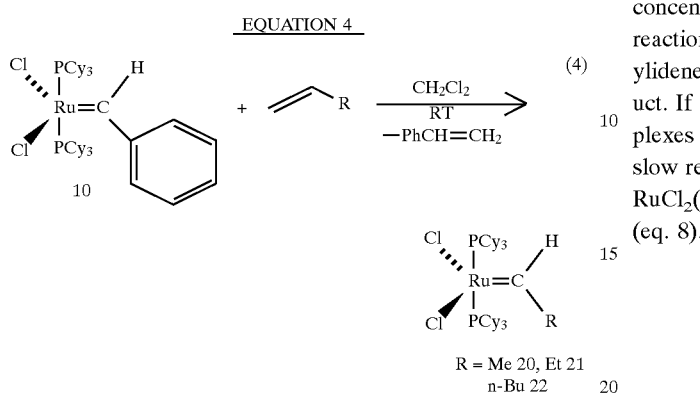

The isolated compounds 20–22 are comparable to precursor complex 10 in stability and solubility and reconvert to precursor complex 10 in the presence of a large excess (30–50 equiv.) of styrene. Metathesis of disubstituted olefins cis-2-butene and cis-3-hexene leads to the formation of $RuCl_2(=CHR)(PCy_3)_2$ from benzylidene complex 10. However, due to the steric bulk of these olefins, the reactions proceed considerably slower than with the corresponding terminal olefins. No reaction occurred between precursor complex 10 and 3,3-dimethyl-1-butene, and stearic interaction between the metal fragment and the incoming olefin is also presumed to be responsible for the slow reaction with 20 equiv. 3-methyl-1-butene. The expected alkylidene $RuCl_2(=CH^iPr)(PCy_3)_2$ was identified by NMR, but its concentration remained small and constant throughout the reaction. After 6 hours, initiation was complete and methylidene complex 19 was isolated as the sole reaction product. If alkylidene forms of $RuCl_2(=CHR)(PCy_3)_2$ of complexes 20–22 are not isolated immediately after formation, slow reaction with excess olefin results in the formation of $RuCl_2(=CH_2)(PCy_3)_2$ (complex 19) within 10–15 hours (eq. 8).

EQUATION 8

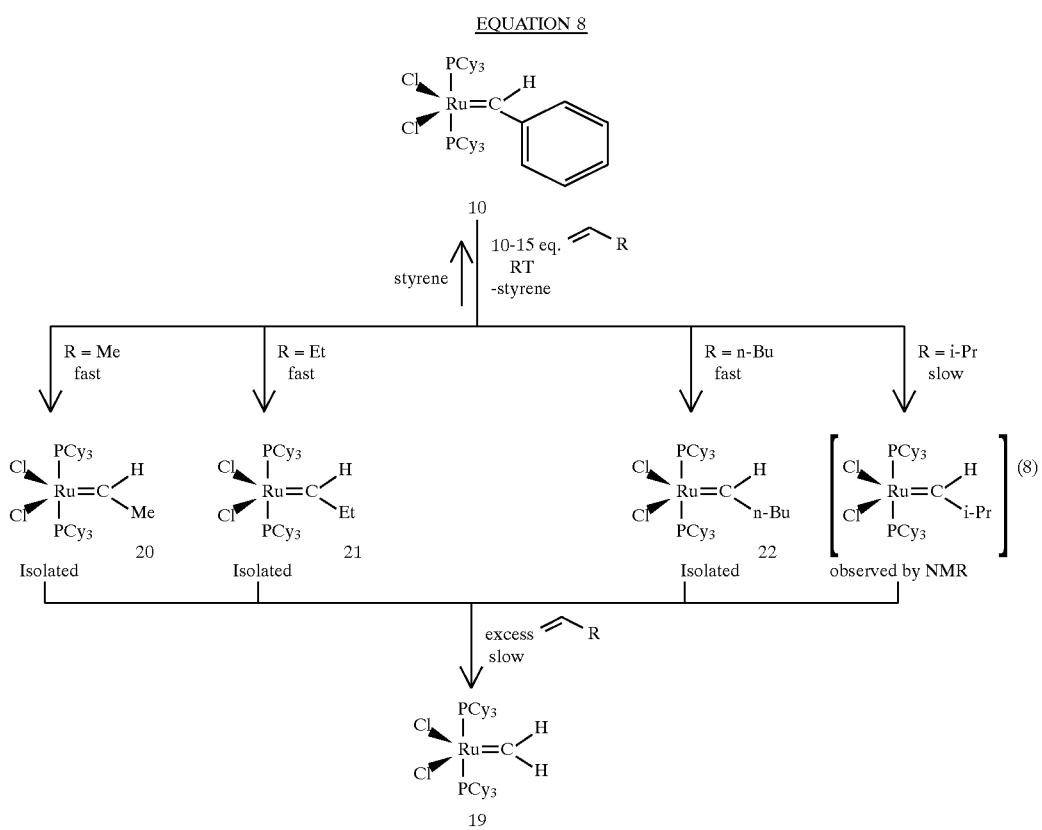

As proposed in the reaction scheme I below, complex 10 is likely to react with a terminal olefin to rapidly form a metallocyclobutane intermediate I, in that the two substituents (Ph and R) are in 1,3-position for stearic reasons. Productive cleavage of the intermediate metallacycle leads to the formation of alkylidene complexes 20–22 as kinetic products.

REACTION SCHEME I

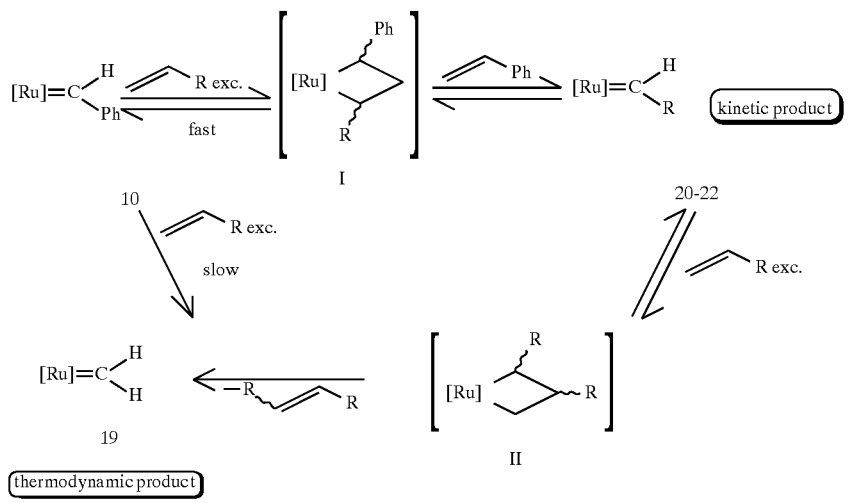

On extended reaction times, alkylidene complexes RuCl$_2$(=CHR)(PCy$_3$)$_2$ (complexes 20–22) undergo a slow reaction with excess olefin to form methylidene complex 19 presumably through intermediate metallocyclobutane II. RuCl$_2$(=CH$_2$)(PCy$_3$)$_2$ (complex 19) appears to be the thermodynamic product as it will not metathesize α-olefins in dilute conditions.

Metathesis of conjugated and cumulated olefins

Treatment of RuCl$_2$(=CHPh)(PCy$_3$)$_2$ (complex 10) with a tenfold excess of 1,3-butadiene and 1,2-propadiene resulted in the high-yield formation of vinylalkylidene RuCl$_2$(=CH—CH=CH$_2$)(PCy$_3$)$_2$ (complex 23) and vinylidene RuCl$_2$(=C=CH$_2$)(PCy$_3$)$_2$ (complex 24), respectively (eq. 5). The former complex cannot be synthesized via ring-opening of cyclopropene.

complexes 23 and 24 exhibit ROMP-activity that, in the case of the former, was evidenced by comparatively slow polymerization of cyclooctene (PDI=2.0). Vinylidene complex 24 rapidly polymerized norbornene, although relatively slow initiation can be inferred by the lack of the characteristic color change, and both compounds are inactive for metathesis of acyclic olefins.

Introduction of functional groups via metathesis

Although less active than their early transition metal counterparts, ruthenium alkylidenes have broader synthetic utility due to their tolerance of functional groups and protic media. The inventors have shown that vinylalkylidenes RuCl$_2$(=CH—CH=CPh$_2$)(PR$_3$)$_2$ (R=Ph, complex A; or R=Cy, complex B) react readily with electron-rich olefins, such as vinyl ethers H$_2$C=CH—OR', to yield metathesis-inactive RuCl$_2$(=CH—OR')(PR$_3$)$_2$. This irreversible reac-

EQUATION 5

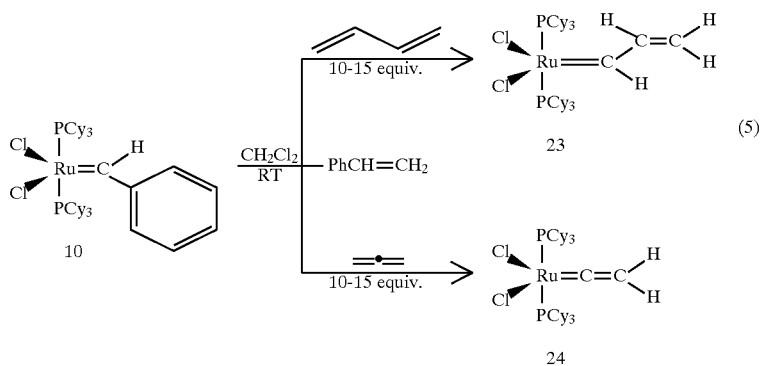

The spectroscopic data for these complexes is similar to those of related compounds RuCl$_2$(=CH—CH=CPh$_2$)(PCy$_3$)$_2$ (complex B) and RuCl$_2$(=C=CH-t-Bu)(PPh$_3$)$_2$. In contrast to observations made in the synthesis of RuCl$_2$(=CHR)(PCy$_3$)$_2$ [R=Me (complex 20), Et (complex 21), n-Bu (complex 22)], that no methylidene RuCl$_2$(=CH$_2$)(PCy$_3$)$_2$ (complex 19) was formed at extended reaction times can be explained by the low activity of complexes 23 and 24 towards their olefinic precursors. However, both tion has been extensively utilized by the inventors for the endcapping of growing polymer chains. Electron-deficient olefins are not metathesized by the triphenylphosphine catalyst RuCl$_2$(=CH—CH=CPh$_2$)(PPh$_3$)$_2$ (complex A), and the tricyclohexylphosphine catalyst RuCl$_2$(=CH—CH=CPh$_2$)(PCy$_3$)$_2$ (complex B) displays only limited activity towards these substrates. However, the enhanced activity of the benzylidene catalyst complex 10 prompted further exploration of this reaction. As shown in eq. 6, metathesis of functionalized olefins catalyzed by benzylidene complex 10 is not limited to electron-rich olefins, such as allyl acetate, but also includes electron-deficient alkenes, such as allyl chloride. Benzylidene complex 10 will also undergo efficient metathesis of unprotected en-ols, as shown with 4-pentene-1-ol, to generate the corresponding hydroxy alkylidene $RuCl_2(=CH(CH_2)_3OH)(PCy_3)_2$ (complex 27) (eq. 6).

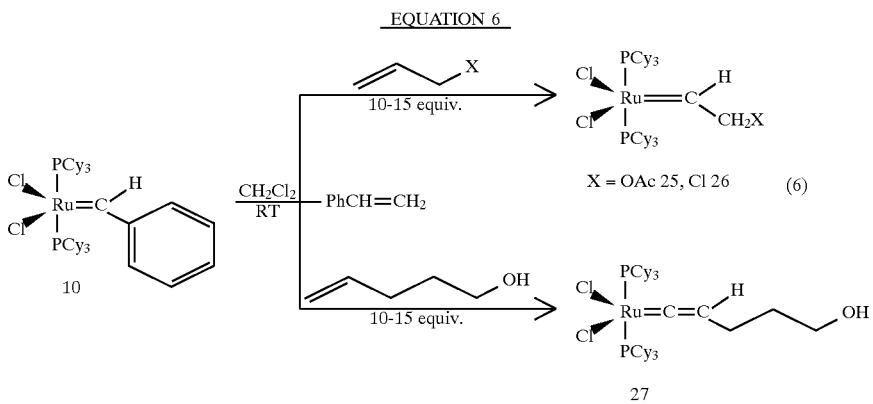

EQUATION 6

Compounds 25–27 were readily isolated and fully characterized. In all cases the alkylidene $H_\alpha$ resonances appeared as triplets due to coupling with the vicinal $CH_2$ groups. Alkylidenes 25–27 are active in ROMP of low strained olefins, which makes them attractive catalysts for the synthesis of telechelic and other functionalized polymers.

USE OF ALKYLIDENE COMPLEXES AS METATHESIS CATALYSTS

Kinetic studies of the polymerization of norborene catalyzed by $RuCl_2(=CH-p-C_6H_4X)(PPh_3)_2$ (Complexes 3–9)

Complexes 3–9 polymerize norbornene at a rate of ≈150 equiv./hour in $CH_2Cl_2$ at RT to give polynorbornene in quantitative yields. All reactions were accompanied by a characteristic color change from green-brown to orange that indicates complete initiation. The resulting polymers are approximately 90% trans as determined by $^1H$ NMR. However, the present catalysts produce nearly monodispersed polymers (PDIs=1.04–1.10, compared to 1.25 for $RuCl_2(=CH—CH=CPh_2)(PPh_3)_2)$ (complex A), consistent with measured initiation rates. As observed for $RuCl_2(=CH—CH=CPh_2)(PPh_3)_2$ (complex A), complexes 3–9 fulfill the general criteria for living systems since the propagating alkylidene ($^1H$ NMR: δ 17.79 ppm (dt)) is stable throughout the reaction, and the molecular weights of the polymers display a linear dependence on the [catalyst]/[monomer] ratio.

The influence of the para-substituents in the alkylidene moiety on the metathesis activity was qualitatively assessed. Catalysts based on complexes 3–9 ($RuCl_2(=CH-p=C_6H_4X)(PPh_3)_2$, [Ru]=0.022M) were treated with norbornene ([monomer]=0.435M) in $CH_2Cl_2$ solution. The pseudo first-order rate constants for initiation and propagation were obtained by integrating the $H_\alpha$ resonances of complexes 3–9 against the corresponding resonance of the propagating alkylidene species, and monitoring the decreasing monomer concentration against an internal ferrocene standard, respectively. The derived values of $k_i$ and $k_p$ are listed in Table III.

TABLE III

| Complex | X | Initiation Rate Constant, $k_i$ ($\times 10^{-3}$/mol · sec) | Propagation Rate Constant, $k_i$ ($\times 10^{-3}$/mol · sec) | $k_i/k_p$ |
|---|---|---|---|---|
| 3 | H | 11.5 | 1.28 | 9.0 |
| 4 | $NMe_2$ | 3.32 | 1.28 | 2.6 |
| 5 | OMe | 3.34 | 1.28 | 2.6 |
| 6 | Me | 3.69 | 1.28 | 2.9 |
| 7 | F | 6.19 | 1.28 | 4.8 |
| 8 | Cl | 1.56 | 1.28 | 1.2 |
| 9 | $NO_2$ | 2.91 | 1.28 | 2.3 | a For [Ru] = 0.022 M;
[norbornene] = 0.435 M in $C_6D_6$ at 17° C.

As can be seen in Table III, the electronic effect of X in $RuCl_2(=CH-p-C_6H_4X)(PPh_3)_2$ on initiation rate seems to be relatively small: the rate in the fastest case (X=H [complex 3]) was approximately 10 times higher than in the slowest (X=Cl [complex 8]). A general trend concerning the electronic influence of the substituents X was not observed. Under similar reaction conditions with $RuCl_2(=CH—CH=CPh_2)(PPh_3)_2$ (complex A) as catalyst, observed initiation was <50%. When norbornene consumption was complete, uninitiated carbene was spectroscopically identified. The extrapolated ratio of $k_i/k_p=6\times10^{-3}$ is approximately 1000 times smaller than that observed for complexes 3–9. These results suggest that conjugation seems to decrease $k_i$, presumably by lowering the ground state energy of the starting arylidenes for complexes 3–9 relative to the likely metallocyclobutane intermediate. Although benzylidene forms of complexes 3–9 are better initiators than $RuCl_2(=CH—CH=CPh_2)(PPh_3)_2$ (Complex A), application of the former as metathesis catalysts is similarly limited to ROMP of relatively high-strained cyclic olefins, such as norbornene and cyclobutene derivatives, whose calculated strain energies exceed 10–15 kcal/mol.

ROMP activity of $RuCl_2(=CH-p-C_6H_4X)(PCy_3)_2$ (complexes 10–16)

Benzylidenes $RuCl_2(=CH-p-C_6H_4X)(PCy_3)_2$ (complexes 10–16) are extremely active ROMP-catalysts compared to their $PPh_3$ analogs complexes 3–9. Except for norbornene, ROMP of highly strained monomers including functionalized norbornenes, 7-oxanorbornenes, and variously substituted cyclobutenes was proved to be living and lead to polymers with exceptionally narrow molecular weight distributions (PDIs <1.1). In analogy to $RuCl_2$ (=CH—CH=$CPh_2$)($PCy_3$)$_2$ (complex B), complexes 10–16 can also polymerize low-strain cycloolefins, such as cyclooctene and 1,5-cyclooctadiene. Although the corresponding polymers are not monodispersed (PDI≈1.50–1.60), these polymerizations proceed more rapidly and with significantly lower polydispersities than with $RuCl_2$(=CH—CH=$CPh_2$)($PCy_3$)$_2$ (complex B) as catalyst (PDI≈2.50). However, the occurrence of "back-biting" in these reactions causes broader PDIs. Therefore, these polymerizations cannot be considered living, even though a propagating alkylidene was observed for ROMP of cyclooctadiene by $^1$H NMR ($\delta$ 18.88 (t)) with complex 10.

Complex 10 also reacts with cyclooctatetraene in $CD_2Cl_2$ with complete initiation, but propagation does not occur, and facile back-biting leads to the formation of benzene. The increased activity of complexes 10–16 compared to $RuCl_2$(=CH—CH=$CPh_2$)($PCy_3$)$_2$ (Complex B) is attributed to a faster initiation rate. Recently developed catalyst mixtures containing [(cymene)$RuCl_2$]$_2$, a bulky tertiary phosphine and trimethylsilyidiazomethane were found to catalyze ROMP of cyclooctenes.

Metathesis of Acyclic Olefins

The inventors recently showed that vinylalkylidene $RuCl_2$(=CH—CH=$CPh_2$)($PCy_3$)$_2$ (Complex B) exhibits metathesis activity towards acyclic olefins, e.g., cis-2-pentene. Although the turnover-numbers were modest compared to the best of the tungsten and molybdenum-based catalysts, vinylalkylidene $RuCl_2$(=CH—CH=$CPh_2$)($PCy_3$)$_2$ (complex B) was the first example of acyclic metathesis induced by a ruthenium carbene complex. However, slow initiation was a present limitation for its general use as a catalyst. Due to their exceptionally high activity in ROMP, complexes 10–16 were found to be efficient acyclic metathesis catalysts, as representatively shown with benzylidene $RuCl_2$(=CHPh)($PCy_3$)$_2$ (complex 10), discussed below.

Kinetic studies with $RuCl_2(=CH-p-C_6H_4X)(PCy_3)_2$ (Complexes 10–16)

Figure 1B:
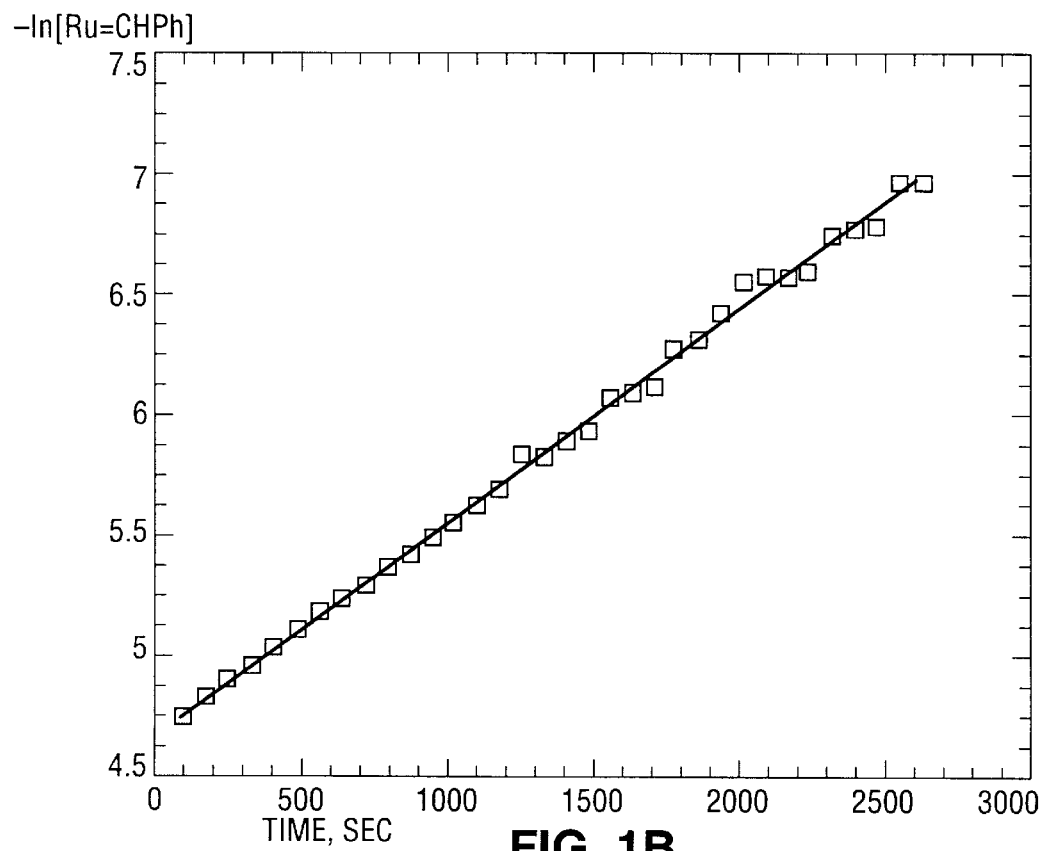

The electronic influence of X on the initiation rates of $RuCl_2(=CH-p-C_6H_4X)(PCy_3)_2$ (complexes 10–16) was probed by examining their reactions with 1-hexene. Clean and quantitative conversion to the pentylidene $RuCl_2$(=CH-n-Bu)($PCy_3$)$_2$ complex 22 was observed in all cases. Pseudo first-order rate constants were measured by integration of the H$\alpha$ resonances of benzylidene complexes 10–16 versus pentylidene complex 22. Representative plots are shown in FIGS. 1A and 1B, and initiation rate constants ($k_i$) are listed in Table IV.

TABLE IV

| Complex | X | Initiation Rate Constant $k_i$ [·10$^{-3}$] (1/mol · sec) |
|---|---|---|
| 10 | H | 2.87 |
| 11 | NMe$_2$ | 0.31 |
| 12 | OMe | 1.01 |
| 3 | Me | 2.15 |
| 14 | F | 1.21 |

TABLE IV-continued

| Complex | X | Initiation Rate Constant $k_i$ [·10$^{-3}$] (1/mol · sec) |
|---|---|---|
| 15 | Cl | 1.37 |
| 16 | NO$_2$ | 1.77 | a For [Ru] = 0.01 M;
[1-hexene] = 0.32 M in $CD_2Cl_2$ at T = 0° C.

As observed for living-ROMP of norbornene with catalysts $RuCl_2(=CH-p-C_6H_4X)(PPh_3)_2$ (complexes 3–9), the range of $k_i$s among the substituted benzylidenes is approximately an order of magnitude. Although no general trend can be discerned, any perturbation to the aromatic $\pi$-system (i.e., X≠H) decreases the initiation rate. $RuCl_2$(=CHPh)($PCy_3$)$_2$ (complex 10) initiated approximately 1000 times faster than vinylidene $RuCl_2$(=CH—CH=$CPh_2$)($PCy_3$)$_2$ (Complex B) which did not completely react to give pentylidene complex 22 under the above-mentioned conditions.

STRUCTURE OF EXEMPLARY COMPLEX
X-ray diffraction study of $RuCl_2(=CH-p-C_6H_4Cl)(PCy_3)_2$ (Complex 15)

Figure 2:
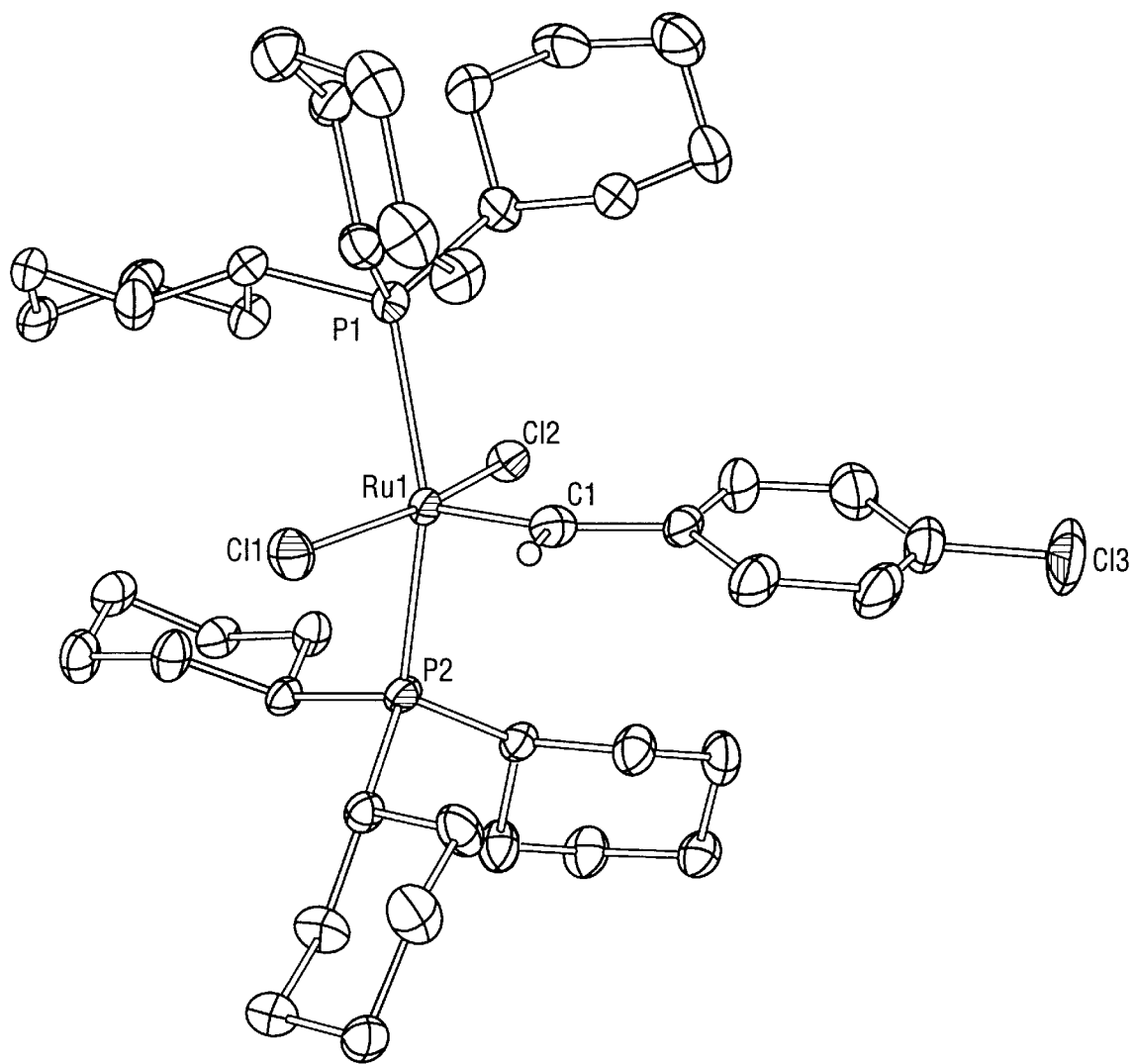
FIG. 2 is an ORTEP plot of $RuCl_2$(=CH-p-$C_6H_4Cl$) $(PCy_3)_2$ (complex 15).

Representative of complexes 10–16, the structure of the Cl— substituted benzylidene $RuCl_2$(=CH-p-$C_6H_4Cl$)($PCy_3$)$_2$ was further confirmed by a single crystal X-ray diffraction study. An ORTEP drawing of this complex is shown in FIG. 2, and selected bond lengths and angles are given in Table V below. The analysis reveals distorted square-pyramidal coordination with a nearly linear Cl(1)-Ru-Cl(2) angle (167.61°). The carbene unit is perpendicular to the P1-Ru-P2 plane, and the aryl ligand is only slightly twisted out of the Cl1-Ru-Cl2 plane. The Ru-C1 bond distance is shorter (1.838(3) Å) than in related compounds $RuCl_2$(=CH—CH=$CPh_2$)($PCy_3$)$_2$ [d(Ru—C)=1.851(21)] or RuCl(=C(OMe)—CH=$CPh_2$)(CO)(Pi-Pr$_3$)$_2$ [$RuCl_2$(=CH—CH=$CPh_2$)($PCy_3$)$_2$F$_4$][d-(Ru—C)=1.874(3), respectively.

TABLE V

| Bond Lengths [Å] | |
|---|---|
| Ru-C1 | 1.839(3) |
| Ru-Cl1 | 2.401(1) |
| Ru-Cl2 | 2.395(1) |
| Ru-P1 | 2.397(1) |
| Ru-P2 | 2.435(1) |
| Cl1-Ru-P1 | 87.2(1) |
| P1-Ru-C1 | 97.5(1) |
| P1-Ru-Cl2 | 91.5(1) |
| Cl1-Ru-P2 | 90.8(1) |
| C1-Ru-P2 | 101.2(1) |
| Cl1-Ru-C1 | 88.7(1) |
| Cl1-Ru-Cl2 | 167.6(1) |
| C1-Ru-Cl2 | 103.7(1) |
| P1-Ru-P2 | 161.1(1) |
| Cl2-Ru-P2 | 86.5(1) |

EXPERIMENTAL SECTION
General Experimental Procedures

All manipulations were performed using standard Schlenk techniques under an atmosphere of argon. Argon was purified by passage through columns of BASF R3-11 catalyst (Chemalog) and 4 Å molecular sieves (Linde). Solid organometallic compounds were transferred and stored in a nitrogen-filled Vacuum Atmospheres drybox or under an atmosphere of argon. NMR spectra were recorded with either a QE-300 Plus (300.1 MHz $^1$H; 75.5 MHz $^{13}$C), a JEOL GX-400 (399.7 MHz $^1$H; 161.9 MHz $^{31}$P) or a Bruker AM 500 (500.1 MHz $^1$H; 125.8 MHz $^{13}$C; 202.5 MHz $^{31}$P; 470.5 MHz $^{19}$F) spectrometer.

Methylene chloride and benzene were passed through columns of activated alumina and stored under argon. Benzene-$d_6$ and methylene chloride-$d_2$ were degassed by three continuous freeze-pump-thaw cycles. RuCl$_2$(PPh$_3$)$_3$, tricyclohexylphosphine, and the diazoalkanes H$_2$CN$_2$, MeCHN$_2$, EtCHN$_2$, PhCHN$_2$, p-C$_6$H$_4$NMe$_2$CHN$_2$, p-C$_6$H$_4$OMeCHN$_2$, p-C$_6$H$_4$MeCHN$_2$, p-C$_6$H$_4$FCHN$_2$, p-C$_6$H$_4$ClCHN$_2$ and p-C$_6$H$_4$NO$_2$CHN$_2$ were prepared according to literature procedures. Norbornene was dried over sodium, vacuum transferred and stored under argon. Cyclooctene, 1,5-cyclooctadiene, and 1,3,5,7-cyclooctatetraene were dried over CaH$_2$, distilled and stored under argon. The following chemicals were obtained from commercial sources and used as received: ethylene, propylene, 1-butene, cis-2-butene, 1-hexene, cis-3-hexene, 3-methyl-1-butene, 3,3-dimethyl-1-butene, 1,3-butadiene, 1,2-propadiene, allyl acetate, allyl chloride, 4-pentene-2-ol, diethyl diallyl malonate, triisopropylphosphine, tricyclopentylphosphine, pentane, ether, acetone, and methanol.

Synthesis of RuCl$_2$(=CHMe)(PPh$_3$)$_2$ and RuCl$_2$(=CHEt)(PPh$_3$)$_2$ (Complexes 1 and 2)

A solution of RuCl$_2$(PPh$_3$)$_3$ (417 mg, 0.43 mmol) in CH$_2$Cl$_2$ (10 mL) was treated at −78° C. with a −50° C. 0.50M solution of diazoethane (1.90 mL, 0.93 mmol, 2.2 eq.) in ether. Upon addition of diazoethane, a color change from orange-brown to green-brown and slight bubbling were observed. After the cooling bath was removed, the solution was stirred for 3 min and then evaporated to dryness. The oily residue was washed several times with small quantities of ice-cold ether (3 mL portions) and the remaining olive-green solid RuCl$_2$(=CHMe)(PPh$_3$)$_2$ was dried under vacuum for several hours. Yield=246 mg (78%). $^1$H NMR (CD$_2$Cl$_2$): δ 18.47 (tq, $J_{PH}$=10.2 Hz, $^3J_{HH}$=5.1 Hz, Ru=CH), 7.68–7.56 and 7.49–7.36 (both m, P(C$_6$H$_5$)$_3$), 2.59 (d, $^3J_{HH}$ 5.1 Hz, CH$_3$). $^{13}$C NMR (CD$_2$Cl$_2$): δ 320.65 (t, $J_{PC}$=9.9 Hz, Ru=CH), 134.76 (m, o-C of P(C$_6$H$_5$)$_3$), 132.06 (m, ipso-C of P(C$_6$H$_5$)$_3$), 130.38 (s, p-C of P(C$_6$H$_5$)$_3$), 128.44 (m, m-C of P(C$_6$H$_5$)$_3$). $^{31}$P NMR (CD$_2$Cl$_2$): δ 29.99 (s, PPh$_3$). Anal. Calcd. for C$_{38}$H$_{34}$Cl$_2$P$_2$Ru: C, 62.99; H, 4.73. Found: C, 63.12; H, 4.61.

In an analogous procedure, RuCl$_2$(=CHEt)(PPh$_3$)$_2$ was prepared, starting with RuCl$_2$(PPh$_3$)$_3$ (502 mg, 0.52 mmol) and a 0.45M solution of diazopropane (2.56 mL, 1.15 mmol, 2.2 eq.) in ether. An orange-brown microcrystalline solid was obtained. Yield=311 mg (81%). $^1$H NMR (C$_6$D$_6$): δ 18.21 (tt, $J_{PH}$=10.8, $^3J_{HH}$ 6.6 Hz, Ru=CH), 7.91–7.86 and 6.97–6.80 (both m, P(C$_6$H$_5$)$_3$), 3.11 (dq, $^3J_{HH}$=$^3J_{HH}$=6.6 Hz, CH$_2$CH$_3$), 0.79 (t, $^3J_{HH}$=6.6 Hz, CH$_2$CH$_3$). $^{13}$C NMR (CD$_2$Cl$_2$): δ 320.88 (t, $J_{PC}$=10.0 Hz, Ru=CH), 134.36 (m, o-C of P(C$_6$H$_5$)$_3$, 132.27 (m. ipso-C of P(C$_6$H$_5$)$_3$), 129.89 (s, p-C of P(C$_6$H$_5$)$_3$), 128.14 (m, m-C of P(C$_6$H$_5$)$_3$), 53.20 (s, CH$_2$CH$_3$), 29.74 (s, CH$_2$CH$_3$). $^{31}$P NMR (CD$_2$Cl$_2$): δ 30.02 (s, PPh$_3$). Anal. Calcd. for C$_{39}$H$_{36}$Cl$_2$P$_2$Ru: C, 63.42; H, 4.91. Found: C, 62.85; H, 4.81.

Synthesis of RuCl$_2$(=CHPh)(PPh$_3$)$_2$ (Complex 3)

A solution of RuCl$_2$(PPh$_3$)$_3$ (2.37 g, 2.47 mmol) in CH$_2$Cl$_2$ (20 mL) was treated at −78° C. with a −50° C. solution of phenyldiazomethane (584 mg, 4.94 mmol, 2.0 eq.) in CH$_2$Cl$_2$ or pentane (3 mL). A spontaneous color change from orange-brown to brown-green and vigorous bubbling were observed. After the cooling bath was removed, the solution was stirred for 5 min and the solution was then concentrated to ~3 mL. Upon addition of pentane (20 mL), a green solid was precipitated, separated from the brown mother-liquid via cannula filtration, dissolved in CH$_2$Cl$_2$ (3 mL) and reprecipitated with pentane. This procedure was repeated until the mother-liquid was nearly colorless. The remaining grey-green microcrystalline solid was dried under vacuum for several hours. Yield=1.67 g (89%). $^1$H NMR (C$_6$D$_6$): δ 19.56 (t, $J_{PH}$=10.2 Hz, Ru=CH), 7.80–7.64 and 6.99–6.66 (both m, C$_6$H$_5$ and P(C$_6$H$_5$)$_3$). $^{13}$C NMR (CD$_2$Cl$_2$): δ 310.12 (t, $J_{PC}$=11.4 Hz, Ru=CH), 155.36 (s, ipso-C of C$_6$H$_5$), 134.91 (m, m-C or o-C of P(C$_6$H$_5$)$_3$), 133.97 (d, $J_{PC}$ 19.6 Hz, ipso-C of P(C$_6$H$_5$)$_3$), 130.44 (s, p-C of P(C$_6$H$_5$)$_3$), 130.03, 128.71 and 127.09 (all s, C$_6$H$_5$), 128.37 (s(br.), m-C or o-C of P(C$_6$H$_5$)$_3$). $^{31}$P NMR (CD$_2$Cl$_2$): δ 30.63 (s, PPh$_3$). Anal. Calcd. for C$_{43}$H$_{36}$Cl$_2$P$_2$Ru: C, 65.65; H, 4.61; P. 7.87. Found: C, 65.83; H, 4.59; P, 7.93.

Synthesis of RuCl$_2$(=CH-p-C$_6$H$_4$NMe$_2$)(PPh$_3$)$_2$ (Complex 4)

A solution of RuCl$_2$(PPh$_3$)$_3$ (466 mg, 0.49 mmol) in CH$_2$Cl$_2$ (10 mL) was treated at −78° C. with a −50° C. solution of p-C$_6$H$_4$NMe$_2$CHN$_2$ (160 mg, 0.98 mmol, 2.0 eq.) in CH$_2$Cl$_2$ (3 mL). A spontaneous color change from orange-brown to brown-green and vigorous bubbling was observed. After the cooling bath was removed, the solution was stirred for 10 min and then the solvent was removed under vacuum. The brown residue was dissolved in minimal amounts of CH$_2$Cl$_2$ (3 mL), and pentane (20 mL) was added to precipitate a green solid. After cannula filtration, this procedure was repeated until the filtrate was colorless. The remaining olive-green microcrystalline solid was dried under vacuum for several hours. Yield=317 mg (78%). $^1$H NMR (CD$_2$Cl$_2$): δ 18.30 (t, $J_{PH}$=6.1 Hz, Ru=CH), 7.64 (d, $^3J_{HH}$=8.7 Hz, o-H of C$_6$H$_4$NMe$_2$), 7.52–7.49 (m, o-H of P(C$_6$H$_5$)$_3$), 7.42 (t, $^3J_{HH}$=7.5 Hz, p-H of P(C$_6$H$_5$)$_3$, 7.33 (t, $^3J_{HH}$=7.5 Hz, m-H of P(C$_6$H$_5$)$_3$), 6.32 (d, $^3J_{HH}$=8.7 Hz, m-H of C$_6$H$_4$NMe$_2$), 2.96 (s, N(CH$_3$)$_2$). $^{13}$C NMR (CD$_2$Cl$_2$): δ 309.68 (t, $J_{PC}$ 11.4 Hz, Ru=CH), 152.72 (s, ipso-C of C$_6$H$_4$NMe$_2$), 135.01 (m, m-C or o-C of P(C$_6$H$_5$)$_3$), 133.57 (s, o-C or m-C of C$_6$H$_4$NMe$_2$), 131.86 (s, C of P(C$_6$H$_5$)$_3$), 130.20 (s, o-C or m-C of C$_6$H$_4$NMe$_2$), 128.27 (m, m-C or o-C of P(C$_6$H$_5$)$_3$), 127.54 (s(br.), p-C of C$_6$H$_4$NMe$_2$), 110.61 (d, $J_{PC}$=21.5 Hz, ipso-C of P(C$_6$H$_5$)$_3$, 40.30 (s, N(CH$_3$)$_2$. $^{31}$P NMR (CD$_2$Cl$_2$): δ 34.84 (s, PPh$_3$). Anal. Calcd. for C$_{45}$H$_{41}$Cl$_2$NP$_2$Ru: C, 65.14; H, 4.98; N, 1.69. Found: C, 65.28; H, 4.97; N 1.80.

Synthesis of RuCl$_2$(=CH-p-C$_6$H$_4$OMe)(PPh$_3$)$_2$ (Complex 5)

A solution of RuCl$_2$(PPh$_3$)$_3$ (561 mg, 0.59 mmol) in CH$_2$Cl$_2$ (12 mL) was treated at −78° C. with a −40° C. solution of p-C$_6$H$_4$OMeCHN$_2$ (87 mg, 0.59 mmol, 1.0 eq.) in CH$_2$Cl$_2$ (3 mL). A spontaneous color change from orange-brown to brown-green and vigorous bubbling was observed. After the cooling bath was removed, the solution was stirred for 5 min and then the solvent was removed under vacuum. The brown-green residue was dissolved in minimal amounts of CH$_2$Cl$_2$ (2 mL), and pentane (20 mL) was added to precipitate a brown solid. The brown-green solution was separated via cannula filtration and dried under vacuum. The remaining olive-green solid, complex 5, was repeatedly washed with ether (10 mL portions) and dried under vacuum for several hours. Yield w. 400 mg (83%). $^1$H NMR (C$_6$D$_6$): δ 19.39 (t, $J_{PH}$=8.7 Hz, Ru=CH), 7.85–7.72 and 7.03–6.80 (both m, C$_6$H$_4$OMe and P(C$_6$H$_5$)$_3$), 6.41 (d, $^3J_{HH}$=8.7 Hz, m-H of C$_6$H$_4$OMe), 3.22 (s, OCH$_3$). $^{13}$C NMR (CD$_2$Cl$_2$); δ 309.20 (t, $J_{PC}$=10.7 Hz, Ru=CH), 147.42 (s, ipso-C of C$_6$H$_4$OMe), 135.56 (pseudo-t, m-C or o-C of P(C$_6$H$_5$)$_3$, 133.98 (s, o-C or m-C of C$_6$H$_4$OMe), 131.46 (s, p-C of P(C$_6$H$_5$)$_3$), 130.43 (s, o-C or m-C of C$_6$H$_4$OMe), 128.40 (pseudo-t, m-C or o-C of P(C$_6$H$_5$)$_3$, 126.82 (s, p-C of $C_6H_4OMe$), 113.95 (d, $J_{PC}$=21.4 Hz, ipso-C of $P(C_6H_5)_3$, 55.77 (s, $OCH_3$). $^{31}P$ NMR ($CD_2Cl_2$): δ 32.50 (s, $PPh_3$). Anal. Calcd. for $C_{44}H_{38}Cl_2OP_2Ru$: C, 64.71; H, 4.69. Found: C, 65.23; H, 4.78.

Synthesis of $RuCl_2(=CH$-p-$C_6H_4Me)(PPh_3)_2$ (Complex 6)

In a technique analogous to that used in synthesizing complex 5, $RuCl_2(=CH$-p-$C_6H_4Me)(PPh_3)_2$ was prepared from $RuCl_2(PPh_3)_3$ (350 mg, 0.37 mmol) and p-$C_6H_4MeCHN_2$ (48 mg, 0.37 mmol, 1.0 eq.) A brown microcrystalline solid was obtained. Yield=258 mg (87%). $^1H$ NMR ($C_6D_6$): δ 19.55 (t, $J_{PH}$=9.6 Hz, Ru=CH), 7.84–7.63 and 7.02–6.80 (both m, $C_6H_4Me$ and $P(C_6H_5)_3$), 6.53 (d, $^3J_{HH}$ 7.8 Hz, m-H of $C_6H_4Me$), 1.68 (s, $CH_3$). $^{13}C$ NMR ($CD_2Cl_2$): δ 309.17 (t, $J_{PC}$=10.9 Hz, Ru=CH), 153.34 (s, ipso-C of $C_6H_4Me$), 135.50 (s, o-C or m-C of $C_6H_4OMe$), 134.96 (m, m-C or o-C of $P(C_6H_5)_3$, 132.13 (s, p-C of $P(C_6H_5)_3$), 130.39 (s, o-C or m-C of $C_6H_4Me$), 128.34 (m, m-C or o-C of $P(C_6H_5)_3$), 126.76 (s, p-C of $C_6H_4Me$), 115.23 (d, $J_{PC}$=21.4 Hz, ipso-C of $P(C_6H_5)_3$), 40.92 (s, $CH_3$). $^{31}P$ NMR ($CD_2Cl_2$): δ 31.29 (s, $PPh_3$). Anal. Calcd. for $C_{44}H_{38}Cl_2P_2Ru$: C, 66.00; H, 4,78. Found: C, 65.90; H, 4.75.

Synthesis of $RuCl_2(=CH$-p-$C_6H_4F)(PPh_3)_2$ (Complex 7)

In a technique analogous to that used in synthesizing complex 3, $RuCl_2(=CH$-p-$C_6H_4F)(PPh_3)_2$ was prepared from $RuCl_2(PPh_3)_3$ (960 mg, 1.00 mmol) and p-$C_6H_4FCHN_2$ (272 mg, 2.00 mmol, 2.0 eg.). Complex 7 was synthesized in analogy to complex 3. An olive-green microcrystalline solid was obtained. Yield=716 mg (89%). $^1H$ NMR ($CD_2Cl_2$): δ 19.24 (t, $J_{PH}$=9.0 Hz, Ru=CH), 7.65–7.62 (m, o-H of $C_6H_4F$), 7.50–7.44 and 7.35–7.32 (both m, $P(C_6H_5)_3$, 6.62 (t, $^3J_{HH}$=$^3J_{HF}$=8.9 Hz, m-H of $C_6H_4F$), 152.21 (s, ipso-C of $C_6H_4F$), 134.95 (m, m-C or o-C of $P(C_6H_5)_3$), 134.04 (d, $J_{CF}$=19.5 Hz, m-C of $C_6H_4F$), 130.56 (s, p-C of $P(C_6H_5)_3$), 130.08 (d, $J_{CF}$=8.7 Hz, o-C of $C_6H_4F$), 128.47 (m, m-C or o-C of $P(C_6H_5)_3$, 115.67 (d, $J_{PC}$=21.8 Hz, ipso-C of $P(C_6H_5)_3$). $^{31}P$ NMR ($CD_2Cl_2$): δ 31.03 (s, $PPh_3$). $^{19}F$ NMR ($CD_2Cl_2$): δ 45.63 (s, $C_6H_4F$). Anal. Calcd. for $C_{43}H_{35}Cl_2FP_2Ru$: C, 64.18; H, 4.38. Found: C, 64.42; H, 4.42.

Synthesis of $RuCl_2(=CH$-p-$C_6H_4Cl)(PPh_3)_2$ (Complex 8)

In a technique analogous to that used in example 2, $RuCl_2(=CH$-p-$C_6H_4Cl)(PPh_3)_2$ was prepared from $RuCl_2(PPh_3)_3$ (350 mg, 0.37 mmol) and p-$C_6H_4ClCHN_2$ (111 mg, 0.73 mmol, 2.0 eq.) A green microcrystalline solid was obtained. Yield=246 mg (82%). $^1H$ NMR ($CD_2Cl_2$); δ 19.27 (t, $J_{PH}$=9.2 Hz, Ru=CH), 7.51–7.44, 7.35–7.32 and 6.67–6.63 (all m, $C_6H_4Cl$ and $P(C_6H_5)_3$), 6.86 (d, $^3J_{HH}$=8.8 Hz, m-H of $C_6H_4Cl$). $^{13}C$ NMR ($CD_2Cl_2$): δ 307.34 (t, $J_{PC}$=10.6 Hz, Ru=CH), 153.82 (s, ipso-C of $C_6H_4Cl$), 134.91 (m, m-C or o-C of $P(C_6H_5)_3$), 130.58 (s, p-C of $P(C_6H_5)_3$, 128.87, 128.81 and 127.85 (all s, $C_6H_4Cl$), 128.48 (s(br.), m-C or o-C of $P(C_6H_5)_3$, 115.90 (d, $J_{PC}$=21.7 Hz, ipso-C of $P(C_6H_5)_3$). $^{31}P$ NMR ($CD_2Cl_2$): δ 30.47 (s, $PPh_3$). Anal. Calcd. for $C_{43}H_{35}C_{13}P_2Ru$: C, 62.90; H, 4.30. Found: C, 62.87; H, 4.40.

Synthesis of $RuCl_2(=CH$-P-$C_6H_4NO_2)(PPh_3)_2$ (Complex 9)

In a technique analogous to that used in synthesizing complex 3, $RuCl_2(=CH$-p-$C_6H_4NO_2)(PPh_3)_2$, complex 9 was prepared from $RuCl_2(PPh_3)_3$ (604 mg, 0.63 mmol) and p-$C_6H_4NO_2CHN_2$ (206 mg, 1.25 mmol, 2.0 eq.) A tan microcrystalline solid was obtained. Yield=398 mg (76%). $^1H$ NMR ($CD_2Cl_2$): δ 19.47 (t, $J_{PH}$=10.8 Hz, Ru=CH), 7.88–7.67, 7.38–7.33 and 7.02–6.71 (all m, $C_6H_4NO_2$ and $P(C_6H_5)_3$. $^{13}C$ NMR ($CD_2Cl_2$): δ 313.43 (t, $J_{PC}$=11.2 Hz, Ru=CH), 158.40 (s, ipso-C of $C_6H_4NO_2$), 148.11 (s, p-C of $C_6H_4NO_2$), 135.49 (m, m-C or o-C of $P(C_6H_5)_3$), 132.21 (s, m-C of $C_6H_4NO_2$), 130.91 (s, p-C of $P(C_6H_5)_3$, 130.72 (s, o-C of $C_6H_4NO_2$), 128.86 (m, m-C or o-C of $P(C_6H_4)_3$, 116.03 (d, $J_{PC}$=21.6 Hz, ipso-C of $P(C_6H_5)_3$). $^{31}P$ NMR ($CD_2Cl_2$): δ 32.27 (s, $PPh_3$). Anal. Calcd. for $C_{43}H_{35}Cl_2NO_2P_2Ru$: C, 62.10; H, 4.24; N, 1.68. Found: C, 62.31; H, 4.66; N, 1.84.

Synthesis of $RuCl_2(=CHPh)(PCy_3)_2$ (Complex 10)

A solution of $RuCl_2(=CHPh)(PPh_3)_2$ (242 mg, 0.31 mmol) in $CH_2Cl_2$ (10 mL) was treated with a solution of tricyclohexylphosphine (190 mg, 0.68 mmol, 2.2 eq.) in $CH_2Cl_2$ (3 mL) and stirred at RT for 30 min. The solution was filtered, and the solvent was removed under vacuum. The residue was repeatedly washed with acetone or methanol (5 mL portions) and dried in vacuo. A purple microcrystalline solid was obtained. Yield 290 mg (89%). $^1H$ NMR ($CD_2Cl_2$): δ 20.02 (s, Ru=CH) (s, Ru=CH), 8.44 (d, $^3J_{HH}$=7.6 Hz, o-H of $C_6H_5$), 7.56 (t, $^3J_{HH}$=7.6 Hz, p-H of $C_6H_5$), 7.33 (t, $^3J_{HH}$=7.6 Hz, m-H of $C_6H_5$), 2.62–2.58, 1.77–1.67, 1.46–1.39 and 1.25–1.16 (all m, $P(C_6H_{11})_3$. $^{13}C$ NMR ($CD_2Cl_2$): δ 294.72 (s, Ru=CH), 153.17 (s, ipso-C of $C_6H_5$), 131.21, 129.49 and 129.27 (all s, $C_6H_5$), 32.49 (pseudo-t, $J_{app}$=9.1 Hz, ipso-C of $P(C_6H_{11})_3$), 30.04 (s, m-C of $P(C_6H_{11})_3$, 28.24 (pseudo-t, $J_{app}$=4.5 Hz, o-C of $P(C_6H_{11})_3$), 26.96 (s, p-C of $P(C_6H_{11})_3$). $^{31}P$ NMR ($CD_2Cl_2$): δ 36.61 (s, $PCy_3$). Anal. Calcd. for $C_{43}H_{72}Cl_2P_2Ru$: C, 62,76; H, 8.82. Found: C, 62.84; H, 8.71.

One-pot Synthesis of $RuCl_2(=CHPh)(PCy_3)_2$ (Complex 10)

A solution of $RuCl_2(PPh_3)_3$ (4.0 g, 4.17 mmol) in $CH_2Cl_2$ (40 mL) was treated at −78° C. with a −50° C. solution of phenyldiazomethane (986 mg, 8.35 mmol, 2.0 eq.) in pentane (10 mL). Upon addition of the diazo compound, an instantaneous color change from orange-brown to green-brown and vigorous bubbling was observed. After the reaction mixture was stirred at −70° C. to −60° C. for 5–10 min, an ice-cold solution of tricyclohexylphosphine (2.57 g, 9.18 mmol, 2.2 eq.) in $CH_2Cl_2$ was added via syringe. Accompanied by a color change from brown-green to red, the solution was allowed to warm to RT and stirred for 30 min. The solution was filtered, concentrated to half of the volume and filtrated. Methanol (100 mL) was added to precipitate a purple microcrystalline solid, complex 10, that was filtered off, washed several times with acetone and methanol (10 mL portions), and dried under vacuum for several hours. Yield 3.40 g (99%).

Synthesis of $RuCl_2(=CH$-p-$C_6H_4NMe_2)(PCy_3)_2$ (Complex 11)

Starting with $RuCl_2(=CH$-p-$C_6H_4NMe_2)(PPh_3)_2$ (316 mg, 0.38 mmol) and tricyclohexylphosphine (235 mg, 0.84 mmol, 2.2 eq.) $RuCl_2(=CH$-p-$C_6H_4NMe_2)(PCy_3)_2$ was obtained as a green microcrystalline solid in a procedure analogous to that used in synthesizing complex 10. Yield 284 mg (86%). $^1H$ NMR ($CD_2Cl_2$): δ18.77 (s, Ru=CH), 8.25–8.14 (s(vbr.), o-H of $C_6H_4NMe_2$), 6.55 (d, $^3J_{HH}$=7.2 Hz, m-H of $C6H_4NMe_2$), 2.97 (s, $N(CH_3)_2$), 2.63–2.61, 1.80–1.67, 1.43–1.41 and 1.21–1.17 (all m, $P(C_6H_{11})_3$). $^{13}C$ NMR ($CD_2Cl_2$): δ 286.13 (s(br.); Ru=CH), 151.28 (s; ipso-C of $C_6H_4NMe_2$), 144.80, 134.85 and 110.50 (all s; $C_6H_4NMe_2$), 40.30 (s, $N(CH_3)_2$, 32.54 (pseudo-t, $J_{app}$=8.2 Hz, ipso-C of $P(C_6H_{11})_3$), 30.10 (s, m-C of $P(C_6H_{11})_3$), 28.36 (m, o-C of $P(C6H_{11})_3$), 27.07 (s, p-C of $P(C_6H_{11})_3$. $^{31}P$ NMR ($CD_2Cl_2$); δ 34.94 (s, $PCy_3$). Anal. Calcd. for $C_{45}H_{77}Cl_2NP_2Ru$: C, 62.41; H, 8.96; N, 1.62. Found: C, 62.87; H, 9.04; N, 1.50.

Synthesis of RuCl$_2$(=CH-p-C$_6$H$_4$OMe)(PCy$_3$)$_2$ (Complex 12)

Starting with RuCl$_2$(=CH-p-C$_6$H$_4$OMe)(PPh$_3$)$_2$ (171 mg, 0.21 mmol) and tricyclohexylphosphine (130 mg, 0.46 mmol, 2.2 eq.), RuCl$_2$(=CH-p-C$_6$H$_4$OMe)(PCy$_3$)$_2$ was obtained as a dark-purple microcrystalline solid, in a technique analogous to that used in synthesizing complex 10. Yield 152 mg (85%). $^1$H NMR (CD$_2$Cl$_2$): δ 19.48 (s, Ru=CH), 8.43 (s(br.), o-H of C$_6$H$_4$OMe), 6.82 (d, $^3J_{HH}$=8.6 Hz, m=H of C$_6$H$_4$OMe), 3.82 (s, OCH$_3$), 2.64–2.59, 1.78–1.68, 1.46–1.39 and 1.26–1.15 (all m, P(C$_6$H$_{11}$)$_3$. $^{13}$C NMR (CD$_2$Cl$_2$); δ 290.90 (s(br.), Ru=CH), 148.34 (s, ipso-C of C$_6$H$_4$OMe), 134.91, 132.30 and 128.83 (all s, C$_6$H$_4$OMe), 55.81 (s, OCH$_3$), 32.51 (pseudo-t, J$_{app}$=9.1 Hz, ipso-C of P(C$_6$H$_{11}$)$_3$), 30.06 (s, m-C of P(C$_6$H$_{11}$)$_3$), 28.28 (pseudo-t, J$_{app}$=5.2 Hz, o-C of P(C$_6$H$_{11}$)$_3$), 27.00 (s, p-C of P(C$_6$H$_{11}$)$_3$). $^{31}$P NMR (CD$_2$Cl$_2$): δ 35.83 (s, PCy$_3$). Anal. Calcd. for C$_{44}$H$_{74}$Cl$_2$OP$_2$Ru: C, 61.96; H, 8.74. Found: C, 62.36; H, 8.71.

Synthesis of RuCl$_2$(=CH-p-C$_6$H$_4$Me)(PCy$_3$)$_2$ (Complex 13)

Starting with RuCl$_2$(=CH-p-C$_6$H$_4$Me(PPh$_3$)$_2$ (416 mg, 0.52 mmol) and tricyclohexylphosphine (321 mg, 1.14 mmol, 2.2 eq.), RuCl$_2$(=CH-p-C$_6$H$_4$Me)(PCy$_3$)$_2$ was obtained as a bright-purple microcrystalline solid, in a technique analogous to that used in synthesizing complex 10. Yield 385 mg (88%). $^1$H NMR(CD$_2$Cl$_2$): δ 19.80 (s, Ru=CH), d, $^3J_{HH}$=7.6 Hz, o-H of C$_6$H$_4$Me), 7.13 (d, $^3J_{HH}$=7.6 Hz, m-H of C$_6$H$_4$Me), 2.08 (s, CH$_3$), 2.62–2.58, 1.77–1.67, 1.43–1.40 and 1.22–1.17 (all m, P(C$_6$H$_{11}$)$_3$). $^{13}$C NMR (CD$_2$Cl$_2$): δ 293.86 (t, J$_{PC}$=8.3 Hz, Ru=CH), 141.48 (s, ipso-C of C$_6$H$_4$Me), 131.56 and 129.85 (both s, C$_6$H$_4$Me), 32.52 (pseudo-t, J$_{app}$=9.2 Hz, ipso-C of P(C$_6$H$_{11}$)$_3$), 30.07 (s, m-C of P(C$_6$H$_{1}$)$_3$), 28.26 (pseudo-t, J$_{app}$=4.1 Hz, o-C of P(C$_6$H$_{11}$)$_3$), 27.00 (s, p-C of P(C$_6$H$_{11}$)$_3$), 22.39 (s, CH$_3$). $^{31}$P NMR (CD$_2$Cl$_2$): δ 36.09 (s, PC$_{y3}$). Anal. Calcd. for C$_{44}$H$_{74}$Cl$_2$P$_2$Ru: C, 63.14; H, 8.91. Found: C, 63.29; H, 8.99.

Synthesis of RuCl$_2$(=CH-p-C$_6$H$_4$F)(PCy$_3$)$_2$ (Complex 14)

Starting with RuCl$_2$(=CH-p-C$_6$H$_4$F)(PPh$_3$)$_2$ (672 mg, 0.84 mmol) and tricyclohexylphosphine (515 mg, 1.84 mmol, 2.2 eq.), RuCl$_2$(=CH-p-C$_6$H$_4$F)(PCy$_3$)$_2$ was obtained as a purple microcrystalline solid, in a technique analogous to that used in synthesizing complex 10. Yield 583 mg (83%). $^1$H NMR (CD$_2$Cl$_2$): δ 19.86 (s, Ru=CH), 8.52–8.50 (s(br.), o-H of C$_6$H$_4$F), 7.00 (dd, $^3J_{HH}$=$^3J_{HF}$=8.8 Hz, m-H of C$_6$H$_4$F), 2.63–2.59, 1.77–1.68, 1.47–1.40 and 1.26–1.17 (all m, P(C$_6$H$_{11}$)$_3$). $^{13}$C NMR(CD$_2$Cl$_2$): δ 291.52 (t, J$_{PC}$=8.6 HZ, Ru=CH), 162.10 (d, J$_{CF}$=254.3 Hz, p-C of C$_6$H$_4$F), 150.57 (s, ipso-C of C$_6$H$_4$F), 134.10 (d, J$_{CF}$=8.9 Hz, o-C of C$_6$H$_4$F), 116.00 (d, J$_{CF}$=21.3 Hz, m-C of C$_6$H$_4$F), 32.49 (pseudo-t, J$_{app}$=9.3 Hz, ipso-C of P(C$_6$H$_{11}$)$_3$), 30.05 (s, m-C of P(C$_6$H$_{11}$)$_3$), 28.22 (pseudo-t, J$_{app}$=5.2 Hz, o-C of P(C$_6$H$_{11}$)$_3$), 26.94 (s, p-C of P(C$_6$H$_{11}$)$_3$. $^{31}$P NMR(CD$_2$Cl$_2$): δ 36.60 (s, PCy$_3$). $^{19}$F NMR(CD$_2$Cl$_2$): δ 45.47 (s, C$_6$H$_4$F). Anal. Calcd. for C$_{43}$H$_{71}$Cl$_2$FP$_2$Ru: C, 61.41; H, 8.51. Found: C, 61.32; H, 8.59.

Synthesis of RuCl$_2$(=CH-p-C$_6$H$_4$Cl)(PCy$_3$)$_2$ (Complex 15)

Starting with RuCl$_2$(=CH-p-C$_6$H$_4$Cl)(PPh$_3$)$_2$ (543 mg, 0.66 mmol) and tricyclohexylphosphine (408 mg, 1.45 mmol, 2.2 eq.), RuCl$_2$(=CH-p-C$_6$H$_4$Cl)(PCy$_3$)$_2$ was obtained as a purple microcrystalline solid in a technique analogous to that used in synthesizing complex 10. Yield 493 mg (87%). $^1$H NMR(CD$_2$Cl$_2$): δ 19.98 (s, Ru=CH), 8.43 (d, $^3J_{HH}$=8.7 Hz, o-H of C$_4$H$_4$Cl), 7.29 (d, $^3J_{HH}$=8.7 Hz, m-H of C$_6$H$_4$Cl), 2.63–2.58, 1.76–1.68, 1.46–1.41 and 1.25–1.17 (all m, P(C$_6$H$_{11}$)$_3$). $^{13}$C NMR(CD$_2$Cl$_2$) (t, J$_{PC}$=8.0 HZ, Ru=CH), 151.81 (s, ipso-C of C$_6$H$_4$Cl), 134.64 (s, p-C of C$_6$H$_4$Cl), 132.56 and 129.51 (both s, o-C and m-C of C$_6$H$_4$Cl), 32.51 (pseudo-t, J$_{app}$=8.9 Hz, ipso-C of P(C$_6$H$_{11}$)$_3$), 30.06 (s, m-C of P(C$_6$H$_{11}$)$_3$), 28.22 (pseudo-t, J$_{app}$=5.2 Hz, o-C of P(C$_6$H$_{11}$)$_3$),26.96 (s, p-C of P(C$_6$H$_{11}$)$_3$). $^{31}$P NMR(CD$_2$Cl$_2$): δ 36.81 (s, PCy$_3$).Anal. Calcd. for C$_{43}$H$_{71}$Cl$_2$FP$_2$Ru: C, 60.24; H, 8.35. Found: C, 60.22; H, 8.45.

Synthesis of RuCl$_2$(=CH-p-C$_6$H$_4$NO$_2$)(PCy$_3$)$_2$ (Complex 16)

Starting with RuCl$_2$(=CH-p-C$_6$H$_4$NO$_2$)(PPh$_3$)$_2$ (609 mg, 0.73 mmol) and tricyclohexylphosphine (452 mg, 1.61 mmol, 2.2 eq.), RuCl$_2$(=CH-p-C$_6$H$_4$NO$_2$)(PCy$_3$)$_2$ was obtained, in a procedure analogous to that in example 11, as a red-purple microcrystalline solid. Yield 527 mg (83%). $^1$H NMR(CD$_2$Cl$_2$): δ 20.71 (s, Ru=CH), 8.64 (d, $^3J_{HH}$=8.4 Hz, o-H of C$_6$H$_4$NO$_2$), 8.13 (d, $^3J_{HH}$=8.4 Hz, of c$_6$h$_4$no$_2$), 2.63–2.58, 1.73–1.68, 1.47–1.40 and 1.26–1.17 (all m, P(C$_6$H$_{11}$)$_3$). $^{13}$C NMR (CD$_2$Cl$_2$) δ 289.07 (t, J$_{PC}$=7.6 Hz, Ru=CH), 155.93 (s, ipso-C of C$_6$H$_4$NO$_2$), 145.34 (s, p-C of C$_6$H$_4$NO$_2$), 131.22 and 125.06 (both s, o-C and m-C of C$_6$H$_4$NO$_2$), 32.57 (pseudo-t, J$_{app}$=9.2 Hz, ipso-C of P(C$_6$H$_{11}$)$_3$), 30.05 (s, m-C of P(C$_6$H$_{11}$)$_3$), 28.16 (pseudo-t, J$_{app}$=4.1 Hz, o-C of P(C$_6$H$_{11}$)$_3$). $^{31}$P NMR(CD$_2$Cl$_2$): δ 38.11 (s, PC$_{y3}$). Anal. Calcd. for C$_{43}$H$_{71}$Cl$_2$NO$_2$P$_2$Ru: C, 59.50; H, 8.25; N, 1.61. Found: C, 59.18; H, 8.25; N, 1.49.

One-pot Synthesis of RuCl$_2$(=CHPh)(PCp$_3$)$_2$ (complex 17)

Complex 17 is obtained in analogy to complex 10 as a purple microcrystalline solid, using RuCl$_2$(PPh$_3$)$_3$ (4.00 g, 4.17 mmol), phenyldiazomethane (986 mg, 8.35 mmol, 2.0 eq.), and tricyclopentyl-phosphine (2.19 g, 9.18 mmol, 2.2. eq.). Due to the better solubility of 17, only methanol is used for the washings. Yield 2.83 g (92%). $^1$H NMR (CD$_2$Cl$_2$): δ 20.20 (s, Ru=CH), 8.47 (d, $^3J_{HH}$=7.5 Hz, o-H of C$_6$H$_5$), 7.63 (t, $^3J_{HH}$=7.5 Hz, p-H of C$_6$H$_5$), 7.36 (t, $^3J_{HH}$=7.5 Hz, m-H of C$_6$H$_5$), 2.68–2.62, 1,81–1.77, 1.62–1.52 and 1.49–1.44 (all m, P(C$_5$H$_9$)$_3$). $^{13}$C NMR (CD$_2$Cl$_2$): δ 300.52 (t, J$_{PC}$=7.6 Hz, Ru=CH), 153.38 (s, ipso-C of C$_6$H$_5$), 130.99, 129.80 and 129.53 (all s, C$_6$H$_5$) 35.54 (pseudo-t, J$_{app}$=11.2 Hz, ipso-C of P(C$_5$H$_9$)$_3$) 29.99 and 26.39 (both s, P(C$_5$H$_9$)$_3$). $^{13}$p NMR (CD$_2$Cl$_2$): δ 29.96 (s, PCp$_3$). Anal. Calcd. for C$_{37}$H$_{60}$Cl$_2$P$_2$Ru: 60.15; H, 8.19. Found: C, 60.39; H, 8.21.

One-pot Synthesis of RuCl$_2$(=CHPh)(PiPr$_3$)$_2$ (complex 18)

Complex 18 is obtained in analogy to complex 17 as a purple microcrystalline solid, using RuCl$_2$(PPh$_3$)$_3$ (4.00 g, 4.17 mmol), phenyldiazomethane (986 mg, 8.35 mmol, 2.0 eq.), and triisopropyl-phosphine (1.79 mL, 9.18 mmol, 2.2. eq.). Yield 2.26 g (93%). $^1$H NMR (CD$_2$Cl$_2$): δ 20.10 (s, Ru=CH), 8.52 (d, $^3J_{HH}$=7.6 Hz, o-H of C$_6$H$_5$), 7.36 (t, $^3J_{HH}$=7.6 Hz, p-H of C$_6$H$_5$), 7.17 (t, $^3J_{HH}$=7.6 Hz, m-H of C$_6$H$_5$), 2.88–2.85, (m, PCHCH$_3$); 1.19 (dvt, N=13.6 Hz, PCHCH$_3$). $^{13}$C NMR (CD$_2$Cl$_2$): δ 296.84 (s(br.), Ru=CH), 152.81 (s, ipso-C of C$_6$H$_5$), 131.37, 129.54 and 129.20 (all s, C$_6$H$_5$) 22.99 (vt, N=$^2$J$_{PC}$+$^4$J$_{PC}$=18.9 Hz, PCHCH$_3$), 19.71 (s, PCHCH$_3$). $^{13}$P NMR (CD$_2$Cl$_2$): δ 45.63 (s, PiPr$_3$). Anal. Calcd. for C$_{25}$H$_{48}$Cl$_2$P$_2$Ru: C, 51.54; H, 8.31. Found: C, 51.69; H, 8.19.

Synthesis of RuCl$_2$(=CH$_2$)(PCy$_3$)$_2$ (Complex 19)

A solution of RuCl$_2$(=CHPh)(PCy$_3$)$_2$ (821 mg, 1.00 mmol) in CH$_2$Cl$_2$ (15 mL) was stirred under an atmosphere of ethylene for 15 min at RT. The solvent was removed under vacuum, the residue repeatedly washed with acetone or pentane (5 mL) and dried under vacuum for several hours. A burgundy microcrystalline solid was obtained. Yield 745 mg (quant.). $^1$H NMR (CD$_2$Cl$_2$): δ 18.94 (s, Ru=CH$_2$), 2.50–2.44, 1.81–1.70, 1.49–1.43 and 1.25–1.23 (all m, P($C_6H_{11}$)$_3$). $^{13}$C NMR (CD$_2$Cl$_2$): δ 294.71 (t, $J_{PC}$=7.6 Hz, $J_{CH}$=164.0 Hz (gated decoupled), Ru=CH), 31.05 (pseudo-t, $J_{app}$=9.6 Hz, ipso-C of P($C_6H_{11}$)$_3$), 29.58 (s, m-C of P($C_6H_{11}$)$_3$), 28.20 (pseudo-t, $J_{app}$=5.3 Hz, o-C of P($C_6H_{11}$)$_3$), 26.94 (s, p-C of P($C_6H_{11}$)$_3$). $^{31}$P NMR (CD$_2$Cl$_2$): δ 43.74 (s, PC$_3$). Anal. Calcd. for C$_{37}$H$_{68}$Cl$_2$P$_2$Ru: C, 59.50; H, 9.18. Found: C, 59.42; H, 9.29.

Synthesis of RuCl$_2$(=CHMe)(PCy$_3$)$_2$ (Complex 20)

In a procedure analogous to that used in synthesizing complex 19, RuCl$_2$(=CHMe)(PCy$_3$)$_2$ was obtained as a red-purple microcrystalline solid, using RuCl$_2$(=CHPh)(PCy$_3$)$_2$ (763 mg, 0.93 mmol) and propylene (or 2-butene) as starting materials. Yield 691 mg (98%). $^1$H NMR (CD$_2$Cl$_2$): δ 19.26 (q, $^3J_{HH}$=5.1 Hz, Ru=CH), 2.57 (d, $^3J_{HH}$=5.1 Hz, CH$_3$), 2.59–2.53, 1.87–1.79, 1.57–1.50 and 1.28–1.23 (all m, P($C_6H_{11}$)$_3$). $^3$C NMR (CD$_2$Cl$_2$): δ 316.32 (t, $J_{PC}$=7.6 Hz, Ru=CH), 49.15 (s, CH$_3$), 32.37 (pseudo-t, $J_{app}$=9.4 Hz, ipso-C of P($C_6H_{11}$)$_3$), 29.87 (s, m-C of P($C_6H_{11}$)$_3$), 28.22 (pseudo-t, $J_{app}$=5.0 Hz, o-C of P($C_6H_{11}$)$_3$), 26.94 (s, p-C of P($C_6H_{11}$)$_3$). $^{31}$P NMR (CD$_2$Cl$_2$): δ 35.54 (s, PCy$_3$). Anal. Calcd. for C$_{38}$H$_{70}$Cl$_2$P$_2$Ru: C, 59.58; H, 9.27. Found: C, 59.91; H, 9.33.

Synthesis of RuCl$_2$(=CHEt)(PCy$_3$)$_2$ (Complex 21)

In a procedure analogous to that used in synthesizing complex 19, RuCl$_2$(=CHEt)(PCy$_3$)$_2$ was obtained as a red-purple microcrystalline solid, using RuCl$_2$(=CHPh)(PCy$_3$)$_2$ and a tenfold excess of 1-butene (or cis-3-hexene) as starting materials. Yield 616 mg (97%). $^1$H NMR (CD$_2$Cl$_2$): δ 19.12 (t, $^3J_{HH}$=5.0 Hz, Ru=CH), 2.79 (dq, $^3J_{HH}$=5.0, $^3J_{HH}$=7.1 Hz, CH$_2$CH$_3$), 2.55–2.49, 1.84–1.81, 1.54–1.47 and 1.26–1.23 (all m, P($C_6H_{11}$)$_3$), 1.35 (t, $^3J_{HH}$=7.1 Hz, CH$_2$CH$_3$). $^{13}$C NMR (CD$_2$Cl$_2$): δ 322.59 (t, $J_{PC}$=9.3 Hz, Ru=CH), 53.48 (s, CH$_2$CH$_3$), 32.20 (pseudo-t, $J_{app}$=8.9 Hz, ipso-C of P($C_6H_{11}$)$_3$), 29.85 (s, m-C of P($C_6H_{11}$)$_3$, 29.57 (s, CH$_2$CH$_3$), 28.22 (pseudo-t, $J_{app}$=4.6 Hz, o-C of P($C_6H_{11}$)$_3$), 26.88 (s, p-C of P($C_6H_{11}$)$_3$. $^{31}$P NMR (CD$_2$Cl$_2$): δ 36.39 (s, PCy$_3$). Anal. Calcd. for C$_{39}$H$_{72}$Cl$_2$P$_2$Ru: C, 60.45; H, 9.37. Found: C, 60.56; H, 9.30.

Synthesis of RuCl$_2$(=CH-n-Bu)(PCy$_3$)$_2$ (Complex 22)

In a procedure analogous to that used in synthesizing complex 19, RuCl$_2$(=CH-n-Bu)(PCy$_3$)$_2$ was obtained as a red-purple microcrystalline solid, using RuCl$_2$(=CHPh)(PCy$_3$)$_2$ (354 mg, 0.43 mmol) and 1-hexene (538 μL, 4.30 mmol, 10 eq.) as starting materials. Yield 328 mg (95%). $^1$H NMR (CD$_2$Cl$_2$); δ 19.24 (t, $^3J_{HH}$=5.1 Hz, Ru=CH), 2.74 (dt, $^3J_{HH}$=5.1, $^3J_{HH'}$=5.2 Hz, (CHCH$_2$), 2.56–2.47, 1.82–1.78, 1.70–1.68, 1.54–1.43, 1.26–1.22 and 0.95–0.86 (all m, CH$_2$CH$_2$CH$_3$ and P($C_6H_{11}$,)$_3$). $^{13}$C NMR (CD$_2$Cl$_2$): δ 321.13 (t, $J_{PC}$=7.6 Hz, Ru=CH), 58.85 (s, CHCH$_2$) 32.25 (pseudo-t, $J_{app}$=9.4 Hz, ipso-C of P($C_6H_{11}$)$_3$), 29.90 (s, m-C of P($C_6H_{11}$)$_3$), 28.23 (pseudo-t, $J_{app}$=5.3 Hz, o-C of P($C_6H_{11}$)$_3$, 26.91 (s, p-C of P($C_6H_{11}$)$_3$), 30.53, 22.94 and 14.06 (all s, CH$_2$CH$_2$CH$_3$). $^{31}$P NMR (CD$_2$Cl$_2$): δ 36.05 (s, PCy$_3$). Anal. Calcd. for C$_{41}$H$_{76}$Cl$_2$P$_2$Ru: C, 61.32; H, 9.54. Found: C, 61.51; H, 9.71.

Synthesis of RuCl$_2$(=CHCH=CH$_2$)(PCy$_3$)$_2$ (Complex 23)

1,3-butadiene is slowly bubbled into a solution of complex 10 (703 mg, 0.85 mmol) in CH$_2$Cl$_2$ (15 mL) for 20 seconds at −20° C. While the solution is allowed to warm to RT within 10 min, a color change from purple to orange-brown is observed. The solvent was removed under vacuum, the residue repeatedly washed with acetone or pentane (5 mL) and dried under vacuum for several hours. A red-purple microcrystalline solid was obtained. Yield 627 mg (95%). $^1$H NMR (CD$_2$Cl$_2$): δ 19.06 (d, $^3J_{HH}$=10.5 Hz, Ru=CH), 8.11 (ddd, $^3J_{HH}$ 10.5, $^3J_{HH}$cis=9.3, $^3J_{HH}$trans=16.8 Hz, CH=CH$_2$), 6.25 (d, $^3J_{HH}$cis=9.3, H$^{cis}$ of CH=CH$_2$), 6.01 (d, $^3J_{HH}$trans=9.3, H$^{trans}$ of CH=CH$_2$), 2.59–2.53, 1.83–1.78, 1.52–1.47 and 1.25–1.21 (all m, P($C_6H_{11}$)$_3$). $^{13}$C NMR (CD$_2$Cl$_2$): δ 296.00 (t, $J_{PC}$ 7.6 Hz. Ru=CH), 153.61 (s, CH=CH$_2$), 115.93 (s, CH=CH$_2$), 32.32 (pseudo-t, $J_{app}$=8.9 Hz, ipso-C of P($C_6H_{11}$)$_3$), 29.82 (s, m-C of P($C_6H_{11}$)$_3$), 28.15 (pseudo-t, $J_{app}$=5.1 Hz, o-C of P($C_6H_{11}$)$_3$), 26.91 (s, p-C of P($C_6H_{11}$)$_3$). $^{31}$P NMR (CD$_2$Cl$_2$): δ 36.17 (s, PCy$_3$). Anal. Calcd. for C$_{39}$H$_{70}$Cl$_2$P$_2$Ru: C, 60.61; H, 9.13. Found: C, 60.79; H, 9.30.

Synthesis of RuCl$_2$(=C=CH$_2$)(PCy$_3$)$_2$ (Complex 24)

In a procedure analogous to that used in synthesizing complex 23, RuCl$_2$(=C=CH$_2$)(PCy$_3$)$_2$ was obtained as a tan microcrystalline solid, using complex 10 (413 mg, 0.50 mmol) and 1,2-propadiene as starting materials. Yield 373 mg (98%). $^1$H NMR (CD$_2$Cl$_2$): δ 3.63 (s, Ru=C=CH$_2$), 2.71–2.64, 2.05–2.01, 1.81–1.53 and 1.32–1.23 (all m, P($C_6H_{11}$)$_3$. $^{13}$C NMR (CD$_2$Cl$_2$): δ 327.41 (t, $J_{PC}$=17.2 Hz, Ru=C=CH$_2$), 99.34 (s, Ru=C=CH$_2$), 33.30 (pseudo=t, $J_{app}$=8.9 Hz, ipso-C of P($C_6H_{11}$)$_3$), 30.41 (s, m-C of P($C_6H_{11}$,)$_3$), 28.32 (pseudo-t, $J_{app}$=5.0 Hz, o-C of P($C_6H_{11}$)$_3$), 27.02 (s, p-C of P($C_6H_{11}$)$_3$). $^{31}$P NMR (CD$_2$Cl$_2$): δ 35.36 (s, PCy$_3$). Anal. Calcd. for C$_{38}$H$_{68}$Cl$_2$P$_2$Ru: C, 60.14; H, 9.03. Found: C, 60.29; H, 8.91.

Synthesis of RuCl$_2$(=CHCH$_2$OAc)(PCy$_3$)$_2$ (Complex 25)

A solution of complex 10 (423 mg, 0.51 mmol) in CH$_2$Cl$_2$ (10 mL) was treated with allyl acetate (555 μL, 5.10 mmol, 10 eq.) at −20° C. While the solution warmed to RT within 10 min, a color change from purple to orange-brown was observed. The solvent was removed under vacuum, the residue repeatedly washed with ice-cold methanol (5 mL portions) and dried under vacuum for several hours. A purple microcrystalline solid, RuCl$_2$(=CHCH$_2$OAc)(PCy$_3$)$_2$, was obtained. Yield 342 mg (83%). $^1$H NMR (CD$_2$Cl$_2$): δ 18.90 (t, $^3J_{HH}$=4.2 Hz, Ru=CH), 4.77 (d, $^3J_{HH}$=3.6 Hz, CH$_2$OAc), 2.09 (s, C(O)CH$_3$), 2.53–2.47, 1.81–1.70, 1.59–1.53 and 1.26–1.22, (all m, P($C_6H_{11}$)$_3$). $^{13}$C NMR (CD$_2$Cl$_2$): δ 305.76 (t, $J_{PC}$=7.6 Hz, Ru=C), 170.41 (s. C(O)CH$_3$), 83.19 (s, CH$_2$OAc), 32.59 (pseudo-t, $J_{app}$=8.6 Hz, ipso-C of P($C_6H_{11}$)$_3$), 29.94 (s, m-C of P($C_6H_{11}$)$_3$), 28.23 (m, o-C of P($C_6H_{11}$)$_3$), 26.91 (s, p-C of P($C_6H_{11}$)$_3$), 20.91 (s, C(O)CH$_3$). $^{31}$P NMR (CD$_2$Cl$_2$): δ 36.66 (s, PCy$_3$). Anal. Calcd. for C$_{39}$H$_{72}$Cl$_2$O$_2$P$_2$Ru: C, 58.05; H, 8.99. Found: C, 58.13; H, 9.07.

Synthesis of RuCl$_2$(=CHCH$_2$Cl)(PCy$_3$)$_2$ (Complex 26)

In a procedure analogous to that used in synthesizing complex RuCl$_2$(=CHCH$_2$Cl)(PCy$_3$)$_2$ was obtained as a purple microcrystalline solid using complex 10 (583 mg, 0.71 mmol) and allyl chloride (577 μL, 7.08 mmol, 10 eq.) as starting materials. Yield 552 mg (80%). $^1$H NMR (CD$_2$Cl$_2$): δ 18.74 (t, $^3J_{HH}$=4.5 Hz, Ru=CH), 4.43(d,$^3J_{HH}$=4.8 Hz, CH$_2$Cl), 2.55–2.50, 1.81–1.70, 1.59–1.52 and 1.27–1.23 (all m, P($C_6H_{11}$)$_3$). $^{13}$C NMR(CD$_2$Cl$_2$): δ 303.00 (t, $J_{PC}$=7.8 Hz, Ru=C), 63.23 (s, CH$_2$Cl), 32.05(pseudo-t, $J_{app}$=8.8 Hz, ipso-C of P($C_6H_{11}$)$_3$), 29.50(s, m-C of P($C_6H_{11}$)$_3$), 27.81(pseudo-t, $J_{app}$=5.2 Hz, o-C of P($C_6H_{11}$)$_3$), 26.56(s, p-C of P($C_6H_{11}$)$_3$). $^{31}$P NMR(CD$_2$Cl$_2$): δ 37.36 (s, PCy$_3$). Anal. Calcd. for C$_{38}$H$_{69}$C$_{13}$P$_2$Ru: C, 57.39; H, 8.74. Found: C, 57.55; H, 8.81.

Synthesis of RuCl$_2$(=CH(CH$_2$)$_3$(OH)(PCy$_3$)$_2$ (Complex 27)

In a procedure analogous to that used in synthesizing complex 25, RuCl$_2$(=CH(CH$_2$)$_3$OH)(PCy$_3$)$_2$ was obtained as a purple microcrystalline solid, using complex 10 (617 mg, 0.82 mmol) and 4-pentene-1-ol (823 μL, 8.2 mmol, 10 eq.) as starting materials. Yield 459 mg (76%). $^1$H NMR (CD$_2$Cl$_2$): δ 19.20 (t, $^3J_{HH}$=4.6 Hz, Ru=CH, 5.46(s(br.), OH), 2.82–2.78, 2.06–2.01 and 1.62–1.58 (all m, CH$_2$CH$_2$CH$_2$OH), 2.55–2.51, 1.84–1.81, 1.55–1.52 and 1.26–1.23 (all m, P(C$_6$H$_{11}$)$_3$). $^{13}$C NMR(CD$_2$Cl$_2$): δ 305.66 5, J$_{PC}$=7.3 Hz, Ru=C, 62.66 (s, CH$_2$OH), 33.01 and 30.08 (both s, CH$_2$CH$_2$) 32.32(pseudo-t, J$_{app}$=8.5 Hz, ipso-C of P(C$_6$H$_{11}$)$_3$), 29.94 (s, m-C of P(C$_6$H$_{11}$)$_3$), 28.28. (pseudo-t, J$_{app}$=5.3 Hz, o-C of P(C$_6$H$_{11}$)$_3$), 26.91 (s, p-C of P(C$_6$H$_{11}$)$_3$). $^{31}$P NMR(CD$_2$Cl$_2$): δ 37.06 (s, PC$_{y3}$). Anal. Calcd. for C$_{40}$H$_{74}$Cl$_2$P$_2$ORu: C, 59.69; H, 9.27. Found: C, 59.51; H, 9.09.

ROMP of Norbornene with Complexes 3–9 as Catalysts

Norbornene (59 mg, 0.63 mmol) was dissolved in CH$_2$Cl$_2$ (0.7 mL) and treated with solutions of complexes 3–9 (6.25 μmol) in CH$_2$Cl$_2$ (0.3 mL) at RT. The reaction mixtures became viscous within 3–5 min and the color changed from brown-green to orange. The solutions were stirred at RT for 1 hour, then exposed to air and treated with CH$_2$Cl$_2$ (2 mL) containing traces of 2,6-di-tert-butyl-4-methylphenol and ethyl vinyl ether. The resulting green solutions were stirred for 20 min and, after filtration through short columns of silica gel, precipitated into vigorously stirred methanol. White, tacky polymers were obtained that were isolated, washed several times with methanol and dried under vacuum. Yields 95–99%, ≈90% trans, M$_n$=31.5–42.3 kg/mol, PDI (toluene): 1.04–1.10.

Determination of Initiation and Propagation Rates in ROMP of Norbornene with Complexes 3–9

1.25×10$^{-5}$ mol of catalysts based on complexes 3–9 were weighed into NMR tubes and dissolved in benzene-d$_6$ (0.3 mL). Ferrocene stock solution in benzene-d$_6$ (20 μL) was added as an internal standard. These mixtures were treated with solutions of norbornene (23.5 mg, 0.25 mmol, 20 eq.) in benzene-d$_6$ (250 μL). A $^1$H NMR-routine was started immediately, taking 60 spectra within 40 min, then 200 spectra within 5 hour. The initiation rate constants (k$_i$) were determined by integration of H$_\alpha$ resonances of the initiating and propagating species. The propagation rate constants (k$_p$) were determined by monitoring the decrease of monomer concentration versus the internal standards. The results are given in Table III (above).

Reaction of Complex 10 with 3-methyl-1-butene and 3,3-dimethyl-1-butene

In individual NMR-tubes, a solution of complex 10 (5.0 mg, 6.1 μmol) in methylene chloride-d$_2$ (0.5 mL) was treated with 10 equiv. 3-methyl-1-butene and 3,3-dimethyl-1-butene (61.0 μmol), respectively. Whereas with the latter reactant, no reaction was observed within 12 hours, a gradual (within 5 min) color change from red-purple to orange indicates that complex 10 undergoes a reaction with 3-methyl-1-butene. Resonances in the $^1$H NMR at δ 18.96 (d, $^3$J$_{HH}$=7.5 Hz, Ru=CHiPr), 2.27 (m, CHCH$_3$) and 1.01 (d, $^3$J$_{HH}$=7.2 Hz, CHCH$_3$) may be attributed to the formation of RuCl$_2$(=CH-i-Pr)(PCy$_3$)$_2$. However, the intensity of these signals did not increase in the course of the reaction, and after 10 min, the corresponding resonances of complex 19 became dominant. ROMP of cyclooctene and 1,5-cyclooctadiene with Complexes 10–16 as Catalysts Complexes 10–16 (6.0 μmol) were individually dissolved in CH$_2$Cl$_2$(0.5 mL) and treated with neat cyclooctene or 1,5-cyclooctadiene (3.0 mmol, 500 eq.) at RT. Accompanied by a color change from purple to orange, the reaction mixtures turned viscous within 3–5 min. The solutions were stirred at RT for 2.5 hour and, upon exposure to air, treated with CH$_2$Cl$_2$(5 mL) containing traces of 2,6-di-tert-butyl-4-methylphenol and ethyl vinyl ether. After 20 min, the viscous solutions were filtered through short columns of silica gel and precipitated into vigorously stirred methanol. The resulting polymers were isolated, washed several times with methanol and dried under vacuum. Cyclooctenamer (white tacky polymers): Yields 95–100%, M$_n$=111–211 kg/mol, PDI (toluene): 1.51–1.63; polybutadiene: (white glue-like polymers): Yields 96–99%, 56–68% cis, M$_n$ 57.9–63.2 kg/mol, PDI (toluene): 1.56–1.67.

Determination of Initiation Rate Constants In Acyclic Metathesis of 1-hexene with Complexes 10–16 as Catalysts 6.05 μmol of catalysts based on complexes 10–16 were placed into NMR tubes and dissolved in methylene chloride-d$_2$ (550 μL). At 0° C. 1-hexene (22.7 μL, 0.18 mmol, 30 eq.) was added and a $^1$H NMR-routine (at 0° C.) was started, taking 60 spectra within 40 min. The initiation rate constants were determined by integration of the H$_\alpha$ resonances of complexes 10–16 and 22. The results are given in Table IV (above).

X-ray Diffraction Study of RuCl$_2$(=CH-p-C$_6$H$_4$Cl)(PCy$_3$)$_2$ (Complex 15)

A maroon prism of complex 15 was obtained by slow diffusion of hexanes into a concentrated solution of complex 15 in methylene chloride (0.5 mL) within 24 hours. A crystal of the size 0.2mm×0.3mm×0.5 mm was selected, oil-mounted on a glass fiber and transferred to a Siemens P4 diffractometer equipped with a modified LT-1 low temperature system. The determination of Laue symmetry, crystal class, unit cell parameters, and the crystal's orientation matrix were carried out according to standard techniques. Low temperature (158K.) intensity data were collected via a 2θ-θ scan technique with MO$_{K\alpha}$ radiation.

All 7782 data were corrected for absorption and for Lorentz and polarization effects and placed on an approximately absolute scale. Any reflection with I(net) <0 was assigned the value |F$_o$|=0. There were no systematic extinctions nor any diffraction symmetry other than the Friedel condition. Refinement of the model proved the centrosymmetric triclinic space group P1 to be the correct choice.

All crystallographic calculations were carried out using either the UCLA Crystallographic Computing Package or the SHELXTL PLUS program. The analytical scattering factors for neutral atoms were used throughout the analysis; both the real (Δf') and imaginary (iΔf") components of anomalous dispersion were included. The quantity minimized during least-squares analysis was Σx(|F$_o$|–|F$_c$|$^2$ where w$^{-1}$=σ$^2$(|F$_o$|)+0.0002(|F$_o$|)$^2$. The structure was solved by direct methods (SHELXTL) and refined by full-matrix least-squares techniques. Hydrogen atoms were located from a difference-Fourier map and included with isotropic temperature parameters. Refinement of the model led to convergence with R$_F$=3.5%, R$_{wF}$=3.6% and GOF=1.42 for 726 variables refined against those 6411 data with |F$_o$|>3.0σ(|F$_o$|)). A final difference-Fourier map yielded ρmax=0.52 e Å$^{-3}$.

What is claimed is:

1. A process for synthesizing a compound of the formula

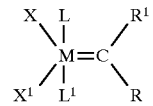

comprising the step of contacting a compound of the formula (XX$^1$ML$_n$L$^1{}_m$)$_p$ with a diazo compound of the formula RC(N$_2$)R$^1$, wherein:

M is selected from the group consisting of Os and Ru;

R and R$^1$ are independently selected from the group consisting of hydrogen, substituted or unsubstituted alkyl, and substituted or unsubstituted aryl;

X and X$^1$ are independently selected from any anionic ligand;

L and $L^1$ are independently selected from any neutral electron donor;

n and m are independently 0–3, provided n+m=3; and p is an integer greater than 0.

2. The process according to claim 1 wherein $R^1$ is hydrogen.

3. A process for synthesizing a compound of the formula

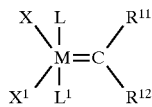

comprising the step of contacting a compound of the formula

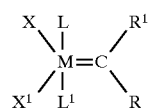

with an olefin of the formula

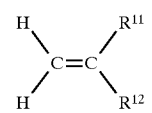

wherein:

M is selected from the group consisting of Os and Ru;

$R^1$ is hydrogen;

R is selected from the group consisting of hydrogen, substituted or unsubstituted alkyl, and substituted or unsubstituted aryl;

$R^{11}$ and $R^{12}$ are independently selected from the group consisting of hydrogen, substituted or unsubstituted alkyl, and substituted or unsubstituted aryl;

X and $X^1$ are independently selected from any anionic ligand; and

L and $L^1$ are independently selected from any neutral electron donor.

4. A process for synthesizing a compound of the formula

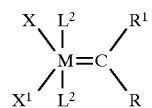

comprising the step of contacting a compound of the formula $(XX^1ML_nL^1_m)_p$ with a diazo compound of the formula $RC(N_2)R^1$ in the presence of a neutral electron donor of the formula $L^2$, wherein:

M is selected from the group consisting of Os and Ru;

R and $R^1$ are independently selected from the group consisting of hydrogen, substituted or unsubstituted alkyl, and substituted or unsubstituted aryl;

X and $X^1$ are independently selected from any anionic ligand;

L, $L^1$, and $L^2$ are independently selected from any neutral electron donor;

n and m are independently 0–3, provided n+m=3; and p is an integer greater than 0.

5. The process according to claims 1 or 4 wherein R includes at least one functional groups selected from the group consisting of alcohol, thiol, ketone, aldehyde, ester, ether, amine, imine, amide, nitro, carboxylic acid, disulfide, carbonate, isocyanate, carbodiimide, carboalkoxy, and halogen.

6. The process according to claims 1 or 4 wherein R is selected from a group consisting of (a) hydrogen;

(b) $C_1$–$C_{20}$ alkyl;

(c) aryl;

(d) $C_1$–$C_{20}$ alkyl substituted with one or more groups selected from the group consisting of aryl, halide, hydroxy, $C_1$–$C_{20}$ alkoxy, and $C_2$–$C_{20}$ alkoxycarbonyl; and (e) aryl substituted with one or more groups selected from the group consisting of $C_1$–$C_{20}$ alkyl, aryl, hydroxyl, $C_1$–$C_5$ alkoxy, amino, nitro, and halide.

7. The process according to any one of claims 1 or 4 wherein R is selected from a group consisting of hydrogen, methyl, ethyl, n-butyl, isopropyl, —$CH_2Cl$, —$CH_2CH_2CH_2OH$, —$CH_2OAc$, unmodified phenyl, and a modified phenyl wherein the phenyl modification is selected from the group consisting of chloride, bromide, iodide, fluoride, —$NO_2$, —$NMe_2$, methoxy, and methyl.

8. The process according to claim 3 wherein $R^{11}$ or $R^{12}$ includes at least one functional groups selected from the group consisting of alcohol, thiol, ketone, aldehyde, ester, ether, amine, imine, amide, nitro, carboxylic acid, disulfide, carbonate, isocyanate, carbodiimide, carboalkoxy, and halogen.

9. The process according to claim 3 wherein $R^{11}$ and $R^{12}$ are each independently selected from a group consisting of (a) hydrogen;

(b) $C_1$–$C_{20}$ alkyl;

(c) aryl;

(d) $C_1$–$C_{20}$ alkyl substituted with one or more groups selected from the group consisting of aryl, halide, hydroxy, $C_1$–$C_{20}$ alkoxy, and $C_2$–$C_{20}$ alkoxycarbonyl; and (e) aryl substituted with one or more groups selected from the group consisting of $C_1$–$C_{20}$ alkyl, aryl, hydroxyl, $C_1$–$C_5$ alkoxy, amino, nitro, and halide.

10. The process according to claim 3 wherein $R^{11}$ and $R^{12}$ are each independently selected from a group consisting of hydrogen, methyl, ethyl, n-butyl, iso-propyl, —$CH_2Cl$, —$CH_2CH_2CH_2OH$, —$CH_2OAc$, unmodified phenyl, and a modified phenyl wherein the phenyl modification is selected from the group consisting of chloride, bromide, iodide, fluoride, —$NO_2$, —$NMe_2$, methoxy, and methyl.

11. The process according to claims 1 or 3 wherein L and $L^1$ are each a phosphine of the formula $PR^3R^4R^5$, wherein $R^3$ is selected from the group consisting of secondary alkyl and cycloalkyl, and $R^4$ and $R^5$ are each independently selected from the group consisting of aryl, $C_1$–$C_{10}$ primary alkyl, secondary alkyl, and cycloalkyl.

12. The process according to claims 1 or 3 wherein L and $L^1$ are each independently selected from the group consisting of -P(cyclohexyl)$_3$, -P(cyclopentyl)$_3$, -P(isopropyl)$_3$, and -P(phenyl)$_3$.

13. The process according to claim 4 wherein L, $L^1$, and $L^2$ are each a phosphine of the formula $PR^3R^4R^5$, wherein $R^3$ is selected from the group consisting of secondary alkyl and cycloalkyl, and $R^4$ and $R^5$ are each independently selected from the group consisting of aryl, $C_1$–$C_{10}$ primary alkyl, secondary alkyl, and cycloalkyl.

14. The process according to claim 4 wherein L, $L^1$, and $L^2$ are each independently selected from the group consisting of -P(cyclohexyl)$_3$, -P(cyclopentyl)$_3$, -P(isopropyl)$_3$, and -P(phenyl)$_3$.

15. The process according to any one of claims 1, 3, and 4 wherein X and $X^1$ are independently selected from the group consisting of hydrogen, halogen, unsubstituted moiety, and substituted moiety wherein the moiety is selected from a group consisting of $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, and $C_1$–$C_{20}$ alkylsulfinyl, and wherein the moiety substitution is selected from a group consisting of $C_1$–$C_5$ alkyl, halogen, $C_1$–$C_5$ alkoxy, unmodified phenyl, halogen substituted phenyl, $C_1$–$C_5$ alkyl substituted phenyl, and $C_1$–$C_5$ alkoxy substituted phenyl.

16. The process according to any one of claims 1, 3, and 4 wherein compound according to claim 13, wherein X and $X^1$ are independently selected from chloride, bromide, iodide, unsubstituted moiety, and substituted moiety wherein the moiety is selected from a group consisting of benzoate, $C_1$–$C_5$ carboxylate, $C_1$–$C_5$ alkyl, phenoxy, $C_1$–$C_5$ alkoxy, $C_1$–$C_5$ alkylthio, arylsulfonate, and $C_1$–$C_5$ alkyl sulfonate, and the moiety substitution is selected from a group consisting of $C_1$–$C_5$ alkyl, unmodified phenyl, halogen substituted phenyl, $C_1$–$C_5$ alkyl substituted phenyl, and $C_1$–$C_5$ alkoxy substituted phenyl.

17. The process according to any one of claims 1, 3, and 4 wherein X and $X^1$ are independently selected from the group consisting of chloride, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate.

18. A process according to claim 2 wherein R and $R^1$ are each independently selected from the group consisting of (a) hydrogen;

(b) $C_1$–$C_4$ alkyl;

(c) phenyl;

(d) $C_1$–$C_4$ alkyl substituted with one or more functional groups selected from the group consisting of halide, hydroxy, and $C_2$–$C_5$ alkoxycarbonyl; and (e) phenyl substituted with one or more functional groups selected from the group consisting of $C_1$–$C_5$ alkyl, $C_1$–$C_5$ alkoxy, amino, nitro, and halide;

X and $X^1$ are each independently selected from the group consisting of Cl, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate; and, L and $L^1$ are each independently selected from the group consisting of -P(phenyl)$_3$, -P(cyclohexyl)$_3$, -P(cyclopentyl)$_3$, and -P(isopropyl)$_3$.

19. The process according to claim 18 wherein $R^1$ is hydrogen;

R is phenyl or a phenyl substituted at the para position with a moiety selected from a group consisting of $C_1$–$C_5$ alkyl, $C_1$–$C_5$ alkoxy, amino, nitro, and halide;

X and $X^1$ are both Cl; and

L and $L^1$ are both -P(cyclohexyl)$_3$.

20. The process according to claim 3 wherein R, $R^{11}$, and $R_{12}$ are each independently selected from a group consisting of (a) hydrogen;

(b) $C_1$–$C_4$ alkyl;

(c) phenyl;

(d) $C_1$–$C_4$ alkyl substituted with one or more functional groups selected from the group consisting of halide, hydroxy, and $C_2$–$C_5$ alkoxycarbonyl; and (e) phenyl substituted with one or more functional groups selected from the group consisting of $C_1$–$C_5$ alkyl, $C_1$–$C_5$ alkoxy, amino, nitro, and halide;

X and $X^1$ are each independently selected from the group consisting of Cl, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate; and, L and $L^1$ are each independently selected from the group consisting of -P(phenyl)$_3$, -P(cyclohexyl)$_3$, -P(cyclopentyl)$_3$, and -P(isopropyl)$_3$.

21. A process according to claim 4 wherein R and $R^1$ is selected from the group consisting of (a) hydrogen;

(b) $C_1$–$C_4$ alkyl;

(c) phenyl;

(d) $C_1$–$C_4$ alkyl substituted with one or more functional groups selected from the group consisting of halide, hydroxy, and $C_2$–$C_5$ alkoxycarbonyl; and (e) phenyl substituted with one or more functional groups selected from the group consisting of $C_1$–$C_5$ alkyl, $C_1$–$C_5$ alkoxy, amino, nitro, and halide;

X and $X^1$ are each independently selected from the group consisting of Cl, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate; and, L, $L^1$, and $L^2$ are each independently selected from the group consisting of -P(phenyl)$_3$, -P(cyclohexyl)$_3$, -P(cyclopentyl)$_3$, and -P(isopropyl)$_3$.

22. The process according to claim 21 wherein $R^1$ is hydrogen;

R is phenyl or a phenyl substituted at the para position with a moiety selected from a group consisting of $C_1$–$C_5$ alkyl, $C_1$–$C_5$ alkoxy, amino, nitro, and halide;

X and $X^1$ are both Cl; and $L^2$ is -P(cyclohexyl)$_3$.

* * * * *

UNITED STATES PATENT AND TRADEMARK OFFICE
CERTIFICATE OF CORRECTION

PATENT NO. : 5,831,108
APPLICATION NO. : 08/693789
DATED : November 3, 1998
INVENTOR(S) : Robert H. Grubbs et al.

It is certified that error appears in the above-identified patent and that said Letters Patent is hereby corrected as shown below:

On title page
Item [75], Inventors:
Insert -- Marcia B. France, Lexington, Virginia --

Signed and Sealed this

Twenty-ninth Day of August, 2006

JON W. DUDAS
*Director of the United States Patent and Trademark Office*

(12) EX PARTE REEXAMINATION CERTIFICATE (5390th)
United States Patent
Grubbs et al.

(10) Number: US 5,831,108 C1
(45) Certificate Issued: Jun. 6, 2006

(54) HIGH METATHESIS ACTIVITY RUTHENIUM AND OSMIUM METAL CARBENE COMPLEXES

(75) Inventors: Robert H. Grubbs, Pasadena, CA (US); Peter Schwab, Bad Durkheim (DE); Sonbinh T. Nguyen, Evanston, IL (US); Marcia B. France, Lexington, VA (US)

(73) Assignees: National Science Foundation, Arlington, VA (US); Nelson D. Abell, III, Monroe, LA (US); APT Aerospace, LLC, Monroe, LA (US); Sterling JA, L.C., Monroe, LA (US)

Reexamination Request:
No. 90/006,939, Feb. 13, 2004

Reexamination Certificate for:
Patent No.: 5,831,108
Issued: Nov. 3, 1998
Appl. No.: 08/693,789
Filed: Jul. 31, 1996

Related U.S. Application Data

(60) Provisional application No. 60/001,862, filed on Aug. 3, 1995, and provisional application No. 60/003,973, filed on Sep. 19, 1995.

(51) Int. Cl.
*C07F 9/00* (2006.01)
*C07F 15/00* (2006.01)

(52) U.S. Cl. .................... 556/21; 556/136; 556/137; 502/152; 502/162

(58) Field of Classification Search .................. None
See application file for complete search history.

(56) References Cited

U.S. PATENT DOCUMENTS 5,750,815 A * 5/1998 Grubbs et al. .............. 585/511

OTHER PUBLICATIONS

France, Marcia Beth; "*Olefin Methathesis with Group VIII Transition Metal Complexes: Mechanism, Reactivity, and Catalyst Development*"; California Institute of Technology, Caltech Libraries No. 3 5047 01260 2652; 1995; 219 Sheets.

* cited by examiner

*Primary Examiner*—Brian Davis

(57) ABSTRACT

Ruthenium and osmium carbene compounds that are stable in the presence of a variety of functional groups and can be used to catalyze olefin metathesis reactions on unstrained cyclic and acyclic olefins are disclosed. Also disclosed are methods of making the carbene compounds. The carbene compounds are of the formula

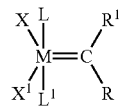

where M is Os or Ru; $R^1$ is hydrogen; R is selected from the group consisting of hydrogen, substituted or unsubstituted alkyl, and substituted or unsubstituted aryl; X and $X^1$ are independently selected from any anionic ligand; and L and $L^1$ are independently selected from any neutral electron donor. The ruthenium and osmium carbene compounds of the present invention may be synthesized using diazo compounds, by neutral electron donor ligand exchange, by cross metathesis, using acetylene, using cumulated olefins, and in a one-pot method using diazo compounds and neutral electron donors. The ruthenium and osmium carbene compounds of the present invention may be used to catalyze olefin metathesis reactions including, but not limited to, ROMP, RCM, depolymerization of unsaturated polymers, synthesis of telechelic polymers, and olefin synthesis.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–22 is confirmed.

* * * * *